(12) United States Patent
Rao

(10) Patent No.: US 12,396,714 B2
(45) Date of Patent: Aug. 26, 2025

(54) SELF-RETAINING SURGICAL RETRACTOR

(71) Applicant: RAO MEDTECH, LLC, Hidden Hills, CA (US)

(72) Inventor: Ramamohan Rao, Hidden Hills, CA (US)

(73) Assignee: RAO MEDTECH, LLC, Hidden Hills, CA (US)

( * ) Notice: Subject to any disclaimer, the term of this patent is extended or adjusted under 35 U.S.C. 154(b) by 302 days.

(21) Appl. No.: 18/141,983

(22) Filed: May 1, 2023

(65) Prior Publication Data
US 2023/0346625 A1 Nov. 2, 2023

Related U.S. Application Data

(60) Provisional application No. 63/337,037, filed on Apr. 29, 2022.

(51) Int. Cl.
| | |
|---|---|
| *A61B 17/02* | (2006.01) |
| *A61B 1/32* | (2006.01) |
| *A61G 13/12* | (2006.01) |

(52) U.S. Cl.
CPC ............... *A61B 17/02* (2013.01); *A61B 1/32* (2013.01); *A61G 13/1245* (2013.01); *A61G 13/129* (2013.01)

(58) Field of Classification Search
CPC .......................... A61G 13/1245; A61G 13/129
See application file for complete search history.

(56) References Cited

U.S. PATENT DOCUMENTS

| | | | | |
|---|---|---|---|---|
| 5,933,887 | A * | 8/1999 | Strange | A61G 13/12 5/624 |
| 9,681,862 | B1 * | 6/2017 | Tumialan | A61B 17/7077 |
| 2013/0303859 | A1 * | 11/2013 | Nowak | A61B 1/32 600/232 |
| 2017/0042527 | A1 * | 2/2017 | Farley | F16B 2/18 |

* cited by examiner

*Primary Examiner* — Tessa M Matthews
(74) *Attorney, Agent, or Firm* — Martin & Ferraro, LLP

(57) ABSTRACT

A self-retaining surgical retractor assembly for use with a patient in a lithotomy position on a surgical table; the retractor assembly comprising a base plate positioned underneath the buttocks of a patient and base plate is held between the patient and a surface of the operating table or examination bed supporting the patient such that the retractor assembly is self-holding; self-stabilizing, and is able to maintain a fixed position relative to patient during use in an examination position while not being attached to the surgical table.

8 Claims, 23 Drawing Sheets

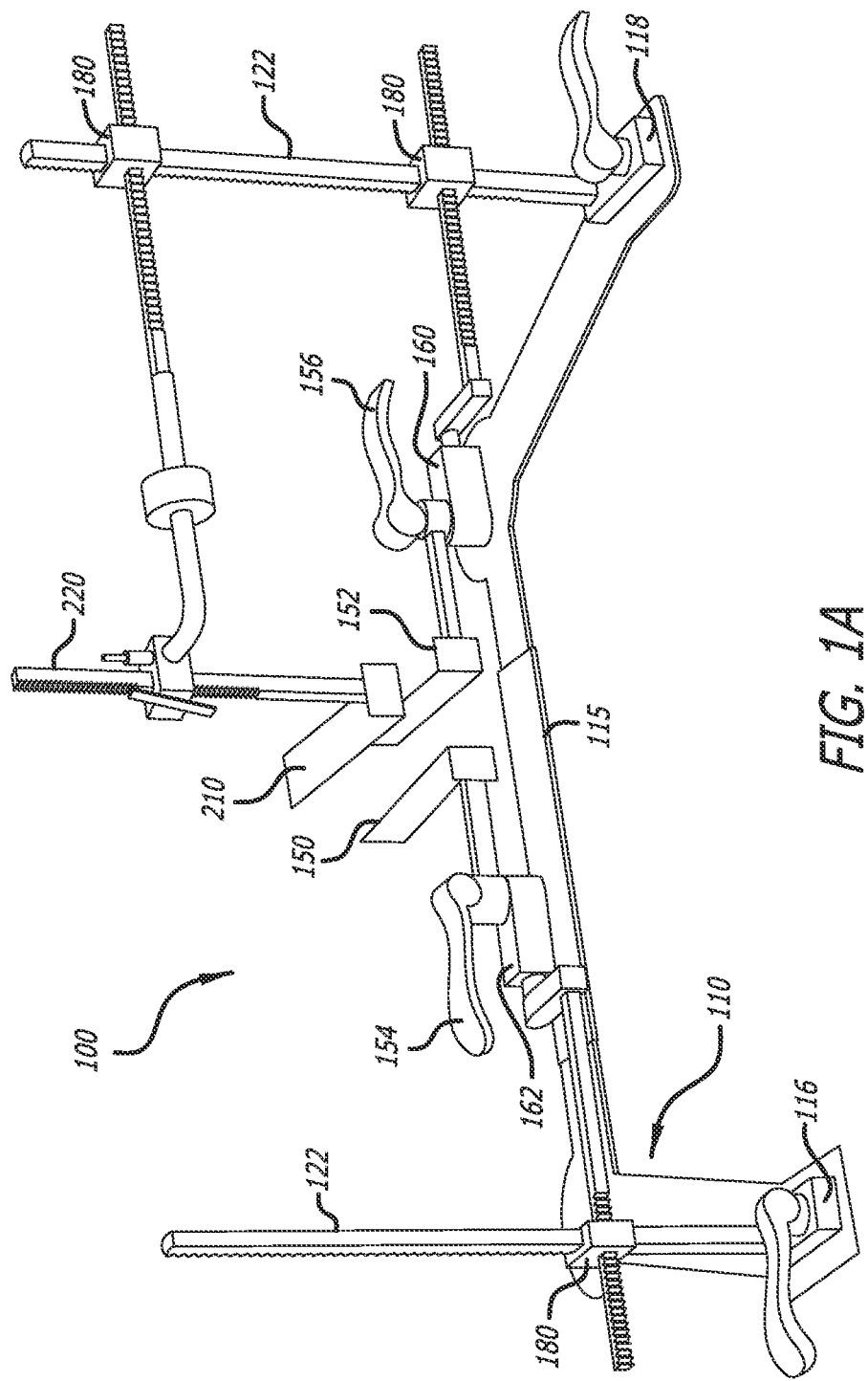

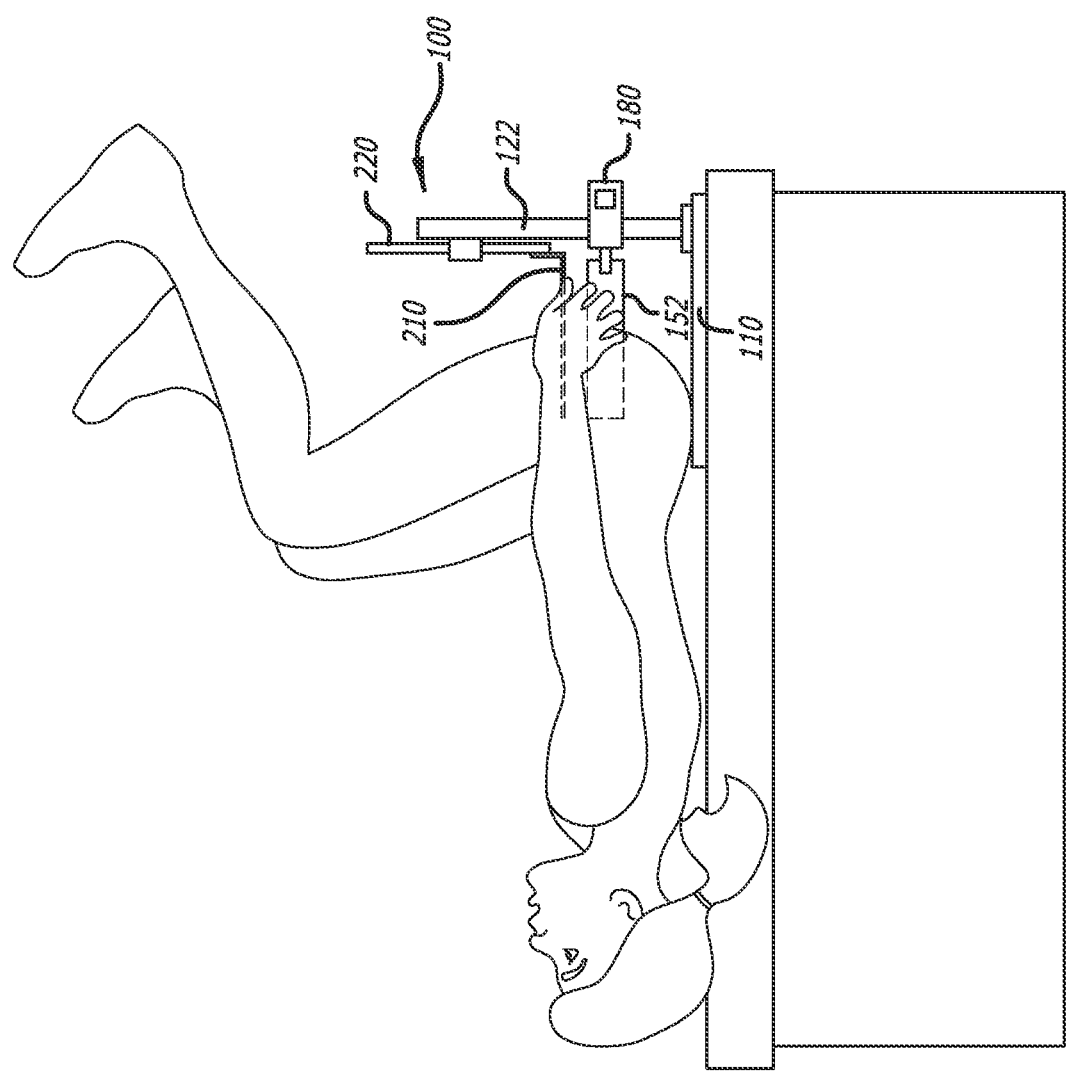

SELF-RETAINING SURGICAL RETRACTOR

CROSS REFERENCES TO RELATED APPLICATIONS

The present application claims the benefit of U.S. provisional patent application No. 63/337,037 filed Apr. 29, 2022 all of which is incorporated by reference herein.

BACKGROUND

Retractors are an integral part of most surgical procedures. Self-retaining surgical retractors, which do not require the assistance of a person to be held in place and properly positioned, are an absolute necessity for any surgeon while doing a very difficult surgery. There are various types of self-retaining retractors in every surgical discipline that provide tremendous help to surgeons during the performance of surgical procedures. It is a mind-numbing job for a person to hold retractors in a cramped up space, often requiring the squeezing of oneself between the limbs of a patient who is in a lithotomy position; and then, trying to follow the direction of the surgeon with minute changes such as to retract further, harder, move the retractor up or down or angle it so that the surgeon has a better view as to where to put the clamp or place a suture. At times of complication that can materialize in no time, for example when assistance is needed at a blink of an eye due to a hemorrhaging blood vessel or a retracted bunch of tissue when the bundle became loose due to a faulty clamp or tissue cut too close to the clamp, the assistants' help plays a major role in accomplishing the complicated surgery and to correct and control complications.

Gynecological surgeries are performed in a restricted narrow tubular surgical field with limited vision of the field and restricted hand movements using long instruments inside the vagina. Vaginal surgeries are difficult to perform because access through the vagina is a major problem due to the anatomy of the vagina which is a tube of tissue approximately 6-8" long and 1-2" in diameter. A majority of gynecological surgeries are done through the vaginal route. These surgeries include vaginal hysterectomies, anterior and posterior bladder and rectal vaginal suspension, excision of certain cysts from the vagina or urethra, tubal surgeries through posterior colpotomy, sling surgeries for bladder neck elevation, cerclage procedures in pregnant women, cervical surgeries like cone biopsy, etc.

A major gynecological surgery team typically includes a surgeon, two assistants (who are either two additional surgeons or physician assistants), a nurse and a circulator. When a major gynecological surgery such as a difficult hysterectomy is performed, it often requires an undivided attention of two assistants standing in compromising postures for 1-2 hours or longer depending on the complexity of the case and ensuing complications. By using a self-retaining retractor at least one of the assistants can be eliminated and the remaining assistant will be able to pay attention to other steps of the procedure such as, for example, to apply and release tissue clamps while sutures are being tied securely. In relatively minor cases like the repair of cystoceles, rectoceles, cone biopsies, or cerclage procedures, a surgeon alone without any assistants will be able to perform the surgery when using the self-retaining retractor. In obstetrics, self-retaining retractors also could play a major benefit in providing ample visual access when there is a major bleed post-delivery resulting from deep sulcus tear or a major laceration to the cervix.

With any gynecological or obstetrical surgery through a vaginal route, the most problematic retractions are the lateral and top portion of the vagina. The bottom portion is not a problem because of the availability of a weighted retractor. A self-retaining retractor's role is to provide the needed retraction on the lateral aspects of the vagina or on the top portion without an assistant and thus reducing the manual labor.

Apart from gynecological surgeons, the self-retaining retractor instrument of the present invention will be useful, for example, to urological surgeons when doing sling surgeries for bladder neck suspension, urethral surgeries, repair of bladder fistulas, etc.

SUMMARY

In one embodiment in accordance with the present invention, a self-retaining surgical retractor assembly for use with a patient in a lithotomy position on a surgical table comprises a plurality of surgical retractors each comprising a blade and a handle; a base plate comprising an upper surface and a lower surface, spaced apart first and second arms each having a leading end and an opposite trailing end, the first and second arms being coupled proximate the leading ends by a connector. The connector having a length that is moveably adjustable to permit modification of a separation distance between the first and second arms, the first and second arms extending from the connector and terminating at the trailing ends. The base plate being sized and configured for placement at least in part on the surgical table and under the patient in the lithotomy position on the surgical table, whereby when the base plate is positioned with the lower surface on the surgical table and the upper surface, the leading ends and connector beneath the buttocks of the patient. The trailing ends of the first and second arms extend to a positon located anterior to the patient to hold instruments at a position in front of the patient.

Left and right lateral vertical arms extend generally perpendicular from the upper surface of the first and second arms of the base plate, the left lateral vertical arm having one end releasably connected to the first arm of the base plate, and the right lateral vertical arm having one end releasably connected to the second arm of the base plate.

A left lower horizontal arm has a central longitudinal axis and a length terminating at an end coupled to a first of the surgical retractors, and a right lower horizontal arm has a central longitudinal axis and a length terminating at an end coupled to a second of the surgical retractors.

An upper horizontal arm has a central longitudinal axis and a length terminating at an end coupled to a third of the surgical retractors.

A first lock has a first portion for movable attachment to the left vertical arm and a second portion for moveable attachment to the left lower horizontal arm. The left lower horizontal arm being held by the first lock in a position with its central longitudinal axis generally perpendicular to the central longitudinal axis of the left vertical arm.

A second lock having a first portion for movable attachment to the right vertical arm and a second portion for moveable attachment to the right lower horizontal arm. The right lower horizontal arm being held by the second lock in a position with its central longitudinal axis generally perpendicular to the central longitudinal axis of the right vertical arm.

A third lock having a first portion for movable attachment to the right vertical arm and a second portion for moveable attachment to the upper horizontal arm. The upper horizontal arm being held by the third lock in a position with its central longitudinal axis generally perpendicular to the central longitudinal axis of the right vertical arm.

Whereby, the vertical positioning of the first, second, and third surgical retractors can be adjusted by movement of the first, second, and third locks up and down along the height of the central axes of the vertical arms, respectively.

Whereby the horizontal positioning of the first, second, and third surgical retractors can be adjusted by movement of the lower and upper horizontal arms along their central axes relative to the first, second, and third locks, respectively.

In another embodiment, the self-retaining surgical retractor assembly for use with a patient in a lithotomy position on a surgical table, the retractor assembly comprises a plurality of surgical retractors each comprising a blade and a handle. A base frame comprising an upper surface and a lower surface, spaced apart first and second arms each having a leading end and an opposite trailing end, the first and second arms being coupled by a rotational connector proximate the leading ends to form a v-shaped configuration, the first and second arms capable of rotational movement about the connector to permit modification of a separation distance between trailing ends of the first and second arms, the first and second arms extending from the connector and terminating at the trailing ends.

A rotating disc positioned above the leading ends of the first and second arms of the base frame over the connector, the rotating disc rotating relative to the base frame and independently of the first and second arms, the rotating disc have an upper surface to be placed in contact with the patient.

The base frame being sized and configured for placement at least in part on the surgical table and under the patient in the lithotomy position on the surgical table. Whereby when the base frame is positioned with the lower surface on the surgical table with the upper surface, the leading ends and the rotating disc beneath the buttocks of the patient, the trailing ends of the first and second arms extend to a positon located anterior to the patient to hold instruments at a position in front of the patient.

Left and right lateral vertical arms extending generally perpendicular from the upper surface of the first and second arms of the base frame, the left lateral vertical arm having one end releasably connected to the first arm of the base frame, the right lateral vertical arm having one end releasably connected to the second arm of the base frame.

A left lower horizontal arm having a central longitudinal axis and a length terminating at an end coupled to a first of the surgical retractors, a right lower horizontal arm having a central longitudinal axis and a length terminating at an end coupled to a second of the surgical retractors.

A first lock having a first portion for movable attachment to the left vertical arm and a second portion for moveable attachment to the left lower horizontal arm, the left lower horizontal arm being held by the first lock in a position with its central longitudinal axis generally perpendicular to the central longitudinal axis of the left vertical arm.

A second lock having a first portion for movable attachment to the right vertical arm and a second portion for moveable attachment to the right lower horizontal arm, the right lower horizontal arm being held by the second lock in a position with its central longitudinal axis generally perpendicular to the central longitudinal axis of the right vertical arm.

Whereby the vertical positioning of the first and second surgical retractors can be adjusted by movement of the first and second locks up and down along the height of the central axes of the vertical arms, respectively, and Whereby the horizontal positioning of the first and second surgical retractors can be adjusted by movement of the lower and upper horizontal arms along their central axes relative to the first and second locks, respectively.

In another embodiment, a self-retaining surgical retractor assembly for use with a patient in a lithotomy position on a surgical table, the retractor assembly comprising a plurality of surgical retractors each comprising a blade and a handle.

A base frame comprising an upper surface and a lower surface, spaced apart first and second arms each having a leading end and an opposite trailing end, the first and second arms being coupled by a rotational connector proximate the leading ends to form a v-shaped configuration, the first and second arms capable of rotational movement about the connector to permit modification of a separation distance between trailing ends of the first and second arms, the first and second arms extending from the connector and terminating at the trailing ends.

A rotating disc positioned above the leading ends of the first and second arms of the base frame over the connector, the rotating disc rotating relative to the base frame and independently of the first and second arms, the rotating disc have an upper surface to be placed in contact with the patient.

The base frame being sized and configured for placement at least in part on the surgical table and under the patient in the lithotomy position on the surgical table, whereby when the base frame is positioned with the lower surface on the surgical table with the upper surface, the leading ends and the rotating disc beneath the buttocks of the patient, the trailing ends of the first and second arms extend to a positon located anterior to the patient to hold instruments at a position in front of the patient.

Left and right lateral vertical arms extending generally perpendicular from the upper surface of the first and second arms of the base frame, the left lateral vertical arm having one end releasably connected to the first arm of the base frame, the right lateral vertical arm having one end releasably connected to the second arm of the base frame.

A ring having an open interior space for accessing a surgical site therethrough, the ring is connected to angled side arms that are also connected to left and right vertical arms.

Retractor blades releasably secured to the ring via sliding locks, retractor blades are positionable along the ring as is suitable for the intended purpose of the surgical procedure being performed.

These and other examples of the present invention will be apparent from review of the following specification and the accompanying drawings.

BRIEF DESCRIPTION OF THE DRAWINGS

The accompanying drawings, which are included to provide further understanding of the present invention disclosed in the present disclosure and are incorporated in and constitute a part of this specification, illustrate aspects of the present invention and together with the description serve to explain the principles of the present invention. In the drawings:

FIG. 1A is a front side perspective view of an assembled self-retaining retractor in accordance with the present invention;

FIG. 1C is a side elevational view of a patient in the lithotomy position positioned on the self-retaining retractor of FIG. 1A and on an operating table;

DETAILED DESCRIPTION

Figure 1B:
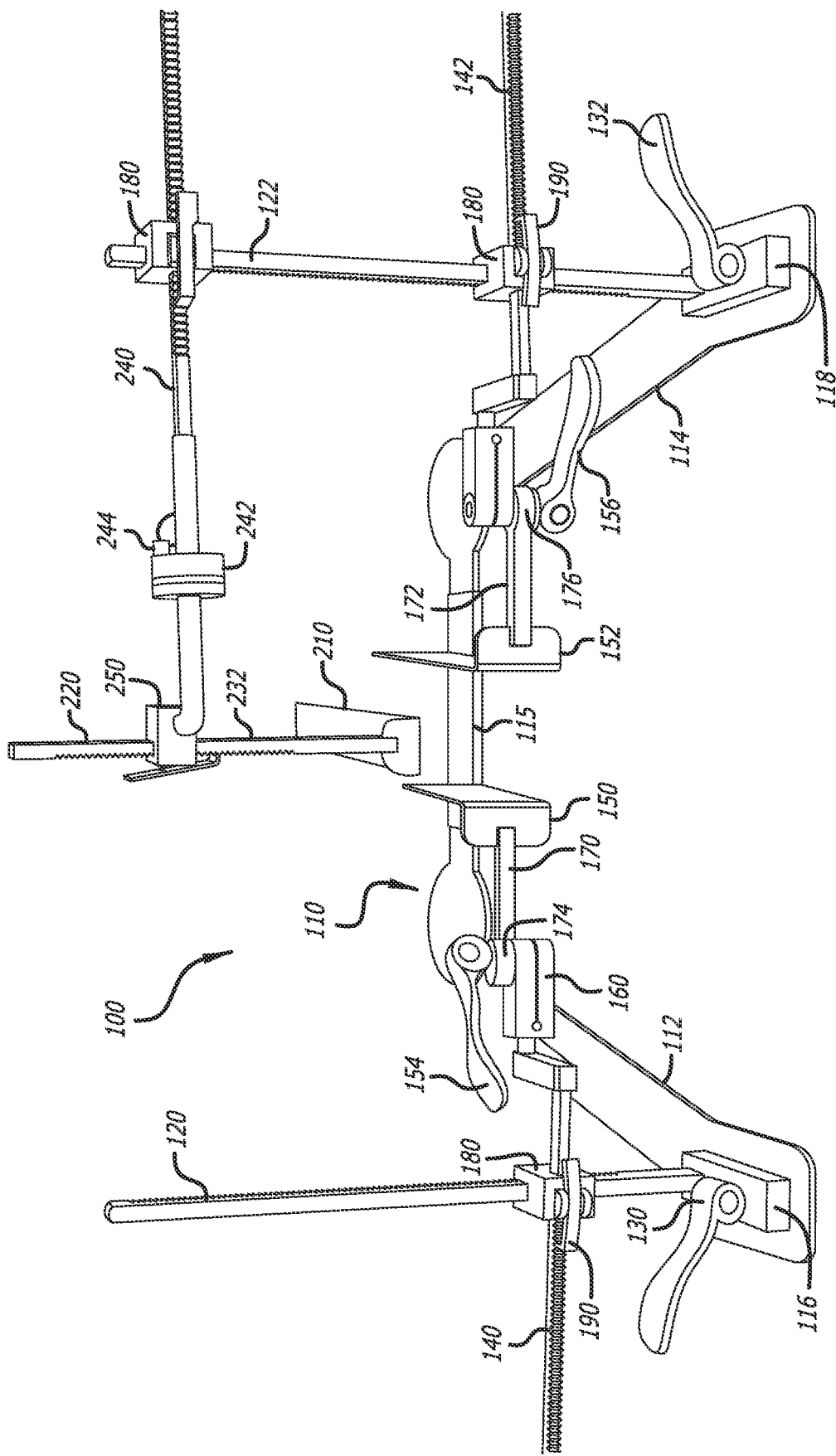
FIG. 1B is a front top perspective view of an assembled self-retaining retractor in accordance with the present invention.

Aspects of the present disclosure are best understood from the following detailed description when read with the accompanying Figures. It is noted that, in accordance with the standard practice in the industry, various features are not drawn to scale. In fact, the dimensions of the various features may be arbitrarily increased or reduced for clarity of discussion.

The following disclosure provides many different embodiments, or examples, for implementing different features of the provided subject matter. Specific examples of components, applications and arrangements are described below to simplify the present disclosure. These are, of course, merely examples and are not intended to be limiting. For example, the attachment of a first feature and a second feature in the description that follows may include embodiments in which the first feature and the second feature are attached in direct contact, and may also include embodiments in which additional features may be positioned between the first feature and the second feature, such that the first feature and the second feature may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Referring to FIGS. 1A-16, an embodiment of a self-retaining retractor assembly (100) in accordance with the present invention is shown. Self-retaining retractor assembly (100) preferably comprises a frame or base plate (110); lateral vertical ratchet arms (120, 122); lower horizontal arms (140, 142); lateral retractor blades (150, 152); lateral blade holders (160, 162); horizontal angular retractor blade (210); central vertical ratchet arm (220); and upper horizontal ratchet arm (240).

As shown in FIGS. 1A-4, a function of base plate (110) is to stabilize retractor assembly (100) during surgery without attaching retractor assembly (100) to the operating room table or any other structures used to support a patient. As shown in FIGS. 1C and 1D, retractor assembly (100) is preferably positioned with base plate (110) underneath the buttocks of a patient, with base plate (110) held between the patient and a surface of the operating table or examination bed supporting the patient. In this manner, utilizing the weight of the patient as a bearing force against base plate (110), retractor assembly (100) is self-holding, self-stabilizing, and is able to maintain a fixed position relative to patient during use in an examination position while not being attached to the surgical table. A significant advantage of the retractor assembly (100) not being attached to the table is to facilitate changes in positioning of the patient without time-consuming dismantling of the device from the surgical table. The self-holding, self-stabilizing, and fixed position relative to the patient reduces or eliminates the need for additional assistants to hold the various retractor blades and other instruments normally handheld during a procedure. In this manner, the physician has unobstructed access to the patient during the examination or surgical procedure and provides clear visualization and optimal exposure to the surgical site.

Figure 1D:
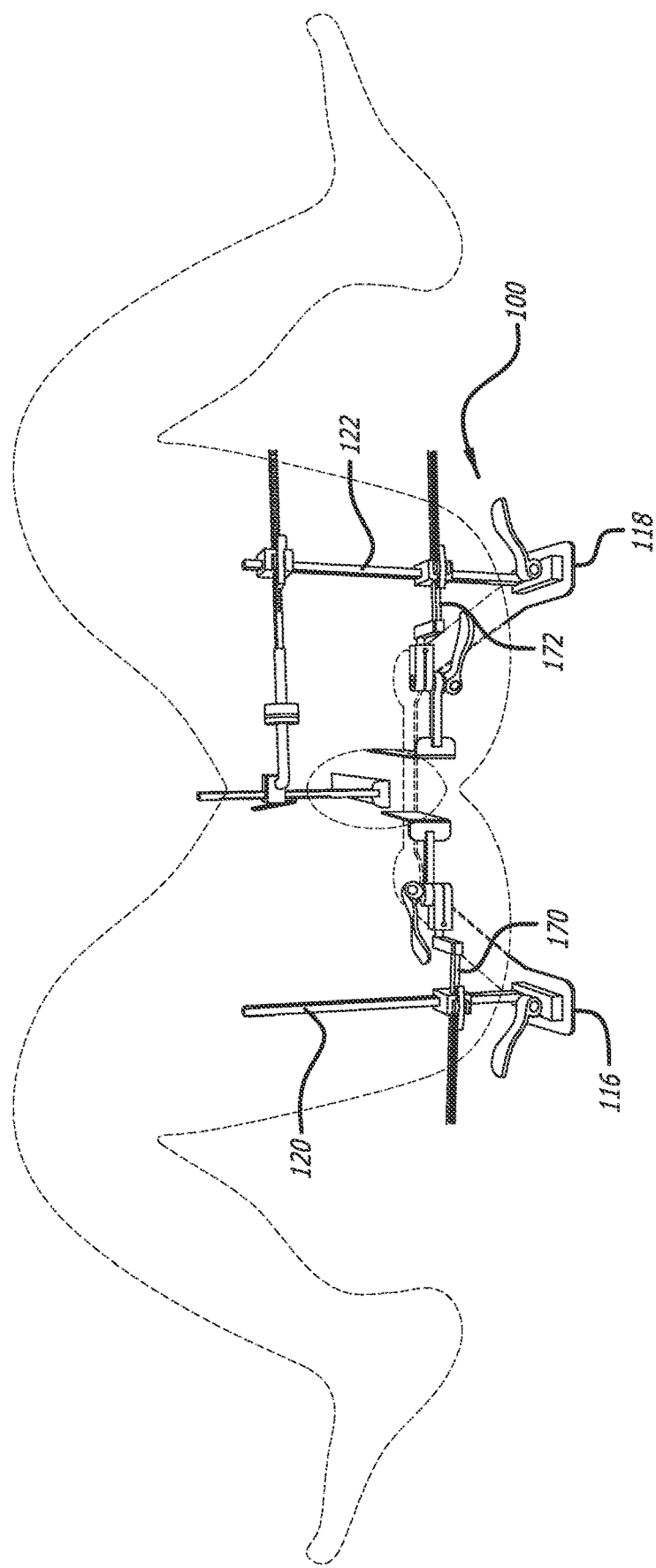
FIG. 1D is a front elevational view of a patient in dotted line shown in the lithotomy position positioned on the self-retaining retractor of FIG. 1A.
Figure 1E:
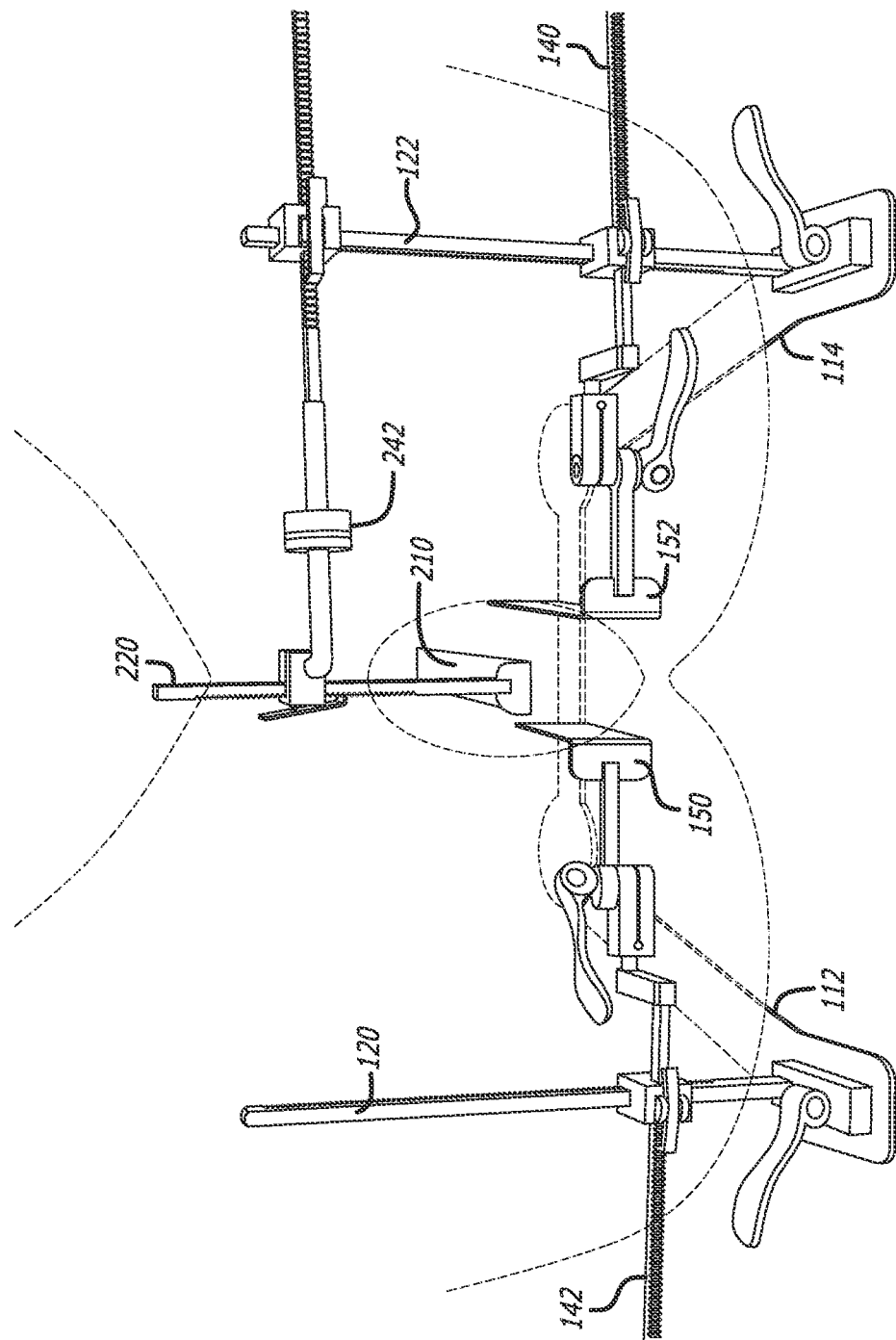
FIG. 1E is an enlarged front elevational view and representative view of a patient in dotted line shown in the lithotomy position positioned on the self-retaining retractor of FIG. 1A.

In use, base plate (110) can be sterilized along with other parts of retractor assembly (100) and then placed under the buttocks of a patient after induction of anesthesia and placing the patient in a lithotomy position as shown in FIGS. 1C-E. To maintain a sterile field, base plate (110) is preferably placed inside a pocket drape and slid under the buttocks of the patient. With at least a portion of the buttocks positioned onto the base plate (110), the weight of the patient maintains surgical retractor assembly (100) in a fixed position relative to the supporting surface (such as the operating table) without requiring additional attachments to the supporting surface. In this manner, surgical retractor assembly (100) is self-retaining and self-positioning relative to the patient while not being fixed to the supporting surface.

In an embodiment of retractor assembly (100), base plate (110) preferably includes an attachment that is preferably an irregular, rectangle-shaped solid piece referred to as fixed base attachments for vertical ratchet arms (116, 118) preferably located at both front ends of base plate (110) for attachment to left and right vertical lateral retractor arms (120, 122). Fixed base attachments (116, 118) preferably include a locking mechanism (130, 132) to lock vertical lateral retractor arms (120, 122) to base plate (110) for stability during a procedure.

Figure 3:
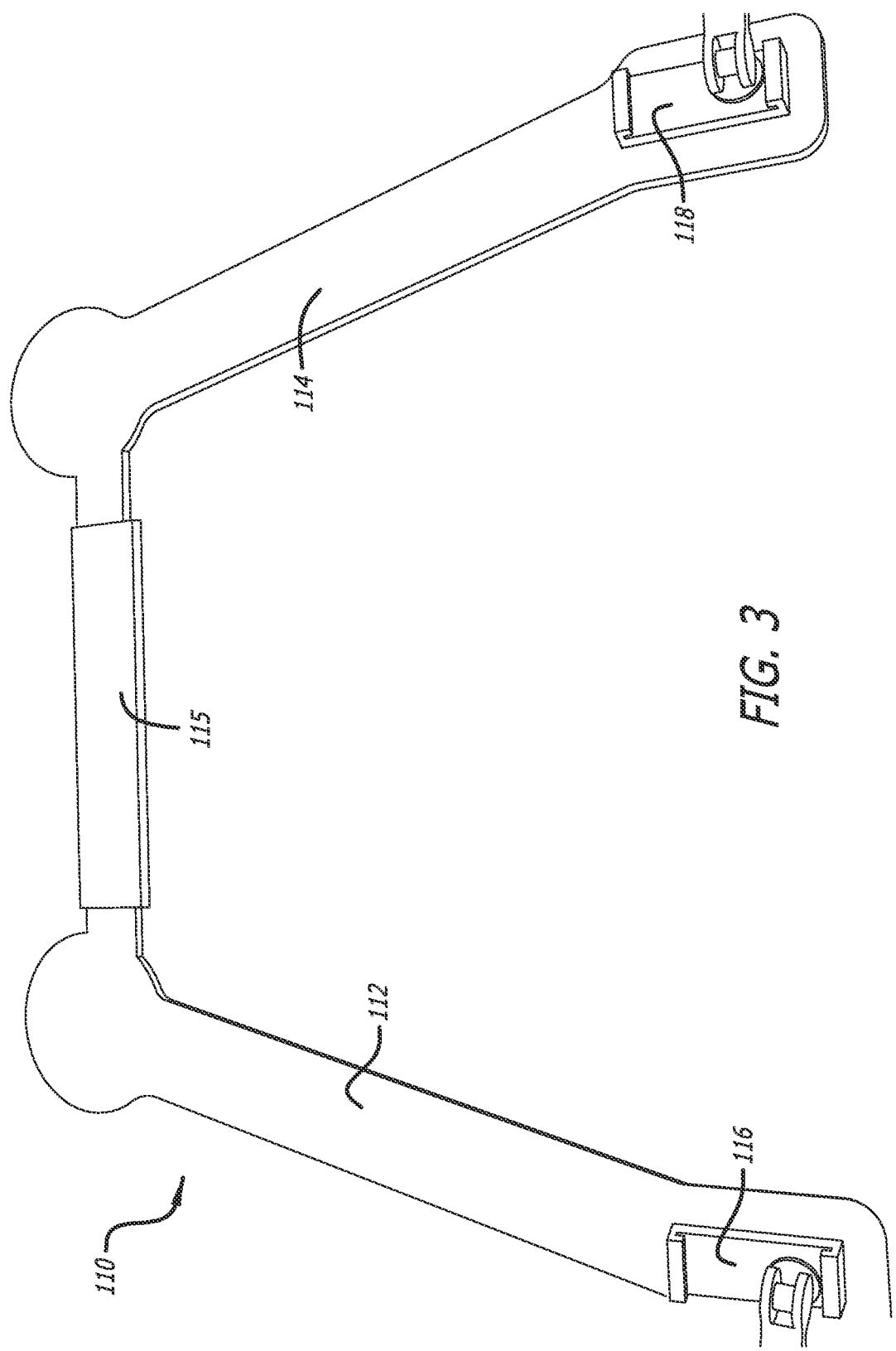
FIG. 3 is a partial top plan view of the base plate of the self-retaining retractor of FIG. 1A.
Figure 4:
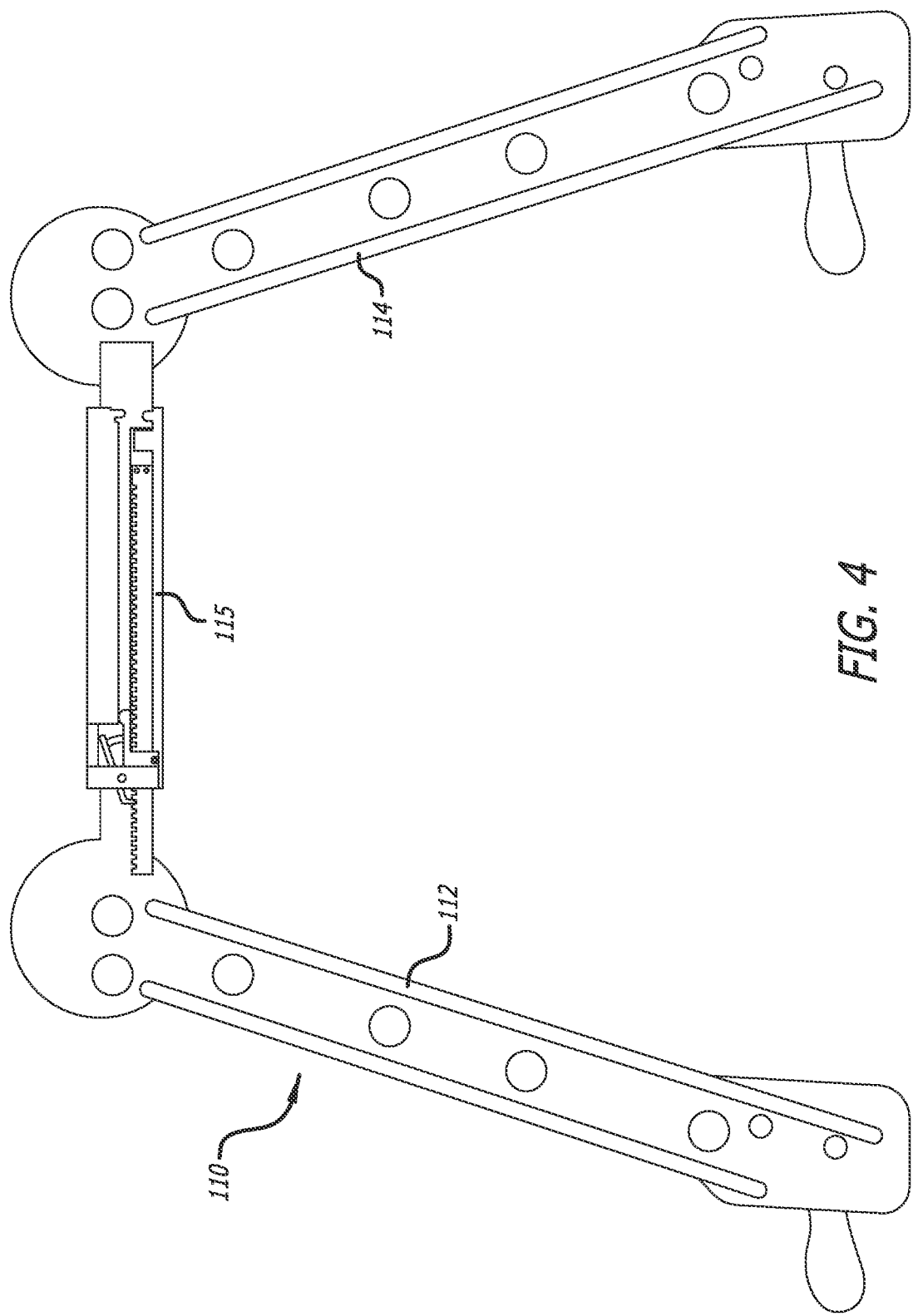
FIG. 4 is a bottom plan view of the base plate of the self-retaining retractor of FIG. 1A.

The width of the base plate (110) between the left and right vertical lateral retractor arms (120, 122) is sufficient to accommodate the hips of a patient on one end, and on the opposite end to span the distance between the legs of patient in an examination position or surgical position. For example, the width of base plate (110) can be modified from approximately 12"-18" depending on the size of the patient and the distance needed between the two vertical lateral retractor arms (120, 122) to access the site of the procedure. As shown in FIGS. 3 and 4, a connector bridge (115) couples together left and right base plate sections (112, 114) by slideable engagement that permits adjustability of base plate (110) to a desired width, and when coupled together to form a generally u-shaped structure.

As shown in FIGS. 1A-1E, 2, and 5, an embodiment of vertical ratchet locks (180) engages left and right vertical retractor arms (120, 122) and are locked into position to base plate (110) by a locking mechanism (130, 132). At the base of the vertical retractor arms (120, 122) are left and right fixed base attachments (116, 118) for vertical retractor arms (120, 122) that are easily slid into position and then locked. Vertical retractor arms (120, 122) are preferably 28.75 cm tall and are preferably solid cubical rods, approximately 0.8 cm in thickness and have ratchets to move left and right lower horizontal arms (140, 142) up and down so that the left and right lateral retractor blades (150, 152) are properly positioned to the desired height during surgery.

Figure 2:
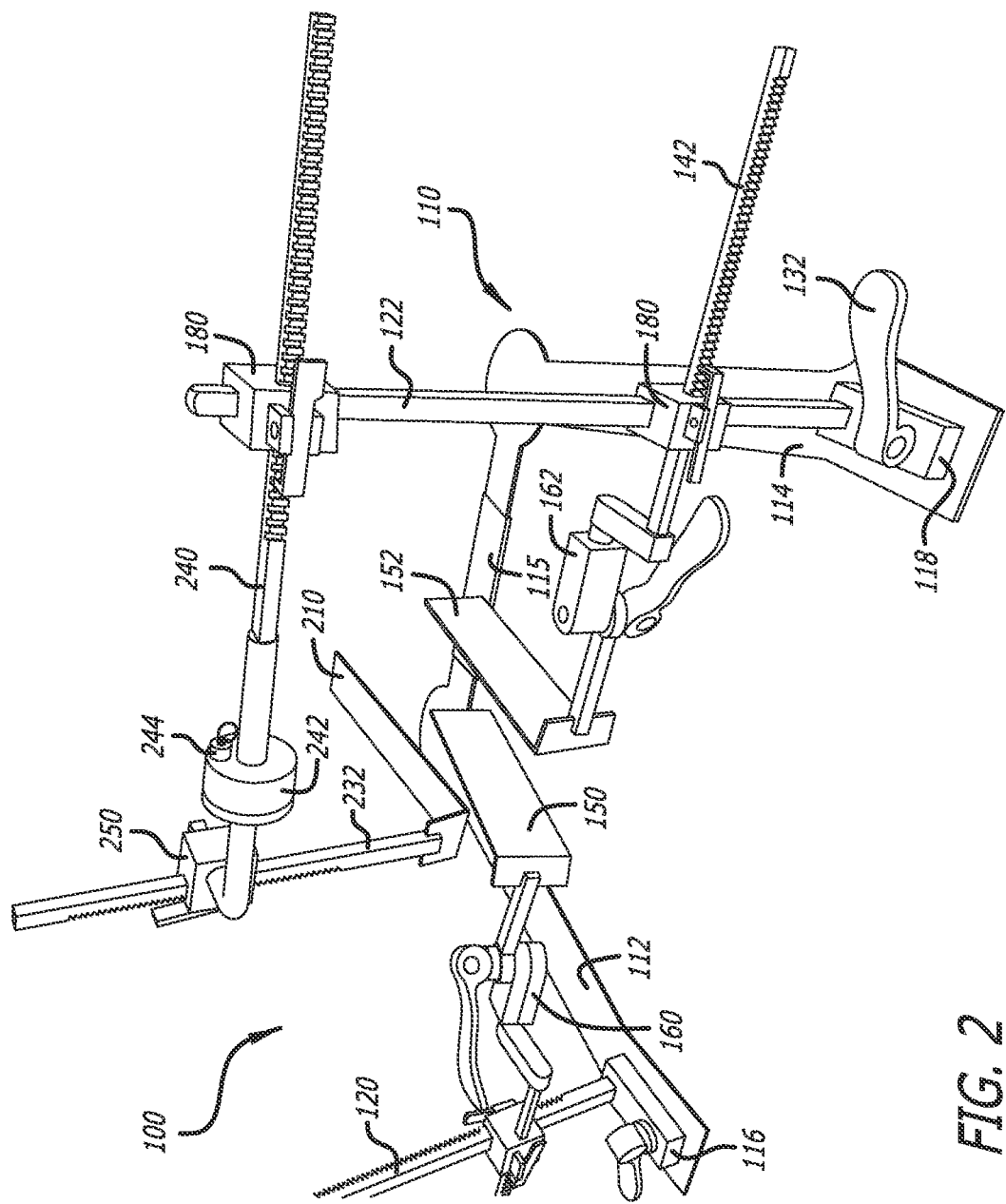
FIG. 2 is a right side perspective view of the self-retaining retractor of FIG. 1A.

As shown in FIGS. 1A, 1B and 2, left and right lateral blade locks (154, 156) preferably comprise a rectangular structure configured for attaching left and right lower horizontal arms (140, 142) that can be locked at a desired distance from the surgical site of a patient such as the vaginal opening. Lateral blade locks (154,156) allow for the movement of lower horizontal arms (140, 142) up or down for a desired height and then lock with locking mechanism (154, 156).

As shown in FIG. 1B, left and right lower horizontal arms (140, 142) are preferably "L"-shaped rods with ratchets to move lateral retractors blades (150, 152) either medially or laterally as needed in adjusting lateral retractor blades (150, 152) during surgery. At the short end of the "L" is a lateral blade holder (160,162) to which lateral retractor blades (150, 152) are removably attached.

As shown in FIGS. 1A, 1B, 2, 5, 8, 10, and 11, lateral blade holder (160, 162) in one embodiment is in the configuration of a rectangular device that is attached to the medial end of lower horizontal arm (140,142). On the top of lateral blade holder (160, 162) preferably is a groove (174, 176) to which handle (170, 172) of lateral retractor blades (150, 152) can be snapped into position and then locked for stability. Releasing left and right lateral blade locks (154, 156) to reposition the lateral retractor blades (150, 152) can be done with a snap. Lateral blade holder (160, 162) has a unique capability to move the tip of lateral retractor blades (150, 152) up and down or toe-it-in as required by the surgeon without removing lateral retractor blade (150, 152) every time by simply releasing lateral blade lock (154, 156), readjusting the position of lateral retractor blade (150, 152) and lock it in a desired position. Left and right retractor blades (150, 152) can be of different sizes and are connected to lateral blade holders (160, 162) through a semi-circular groove (174, 176) at the lateral tip of handle (170, 172) so that it can be locked into position with ease through lateral blade lock (154, 156). As used in this description, retractor blades include vaginal retractors and also other types of surgical retractors that may be suitable for their intended use with the surgical retractor assembly in accordance with the present invention.

Figure 14:
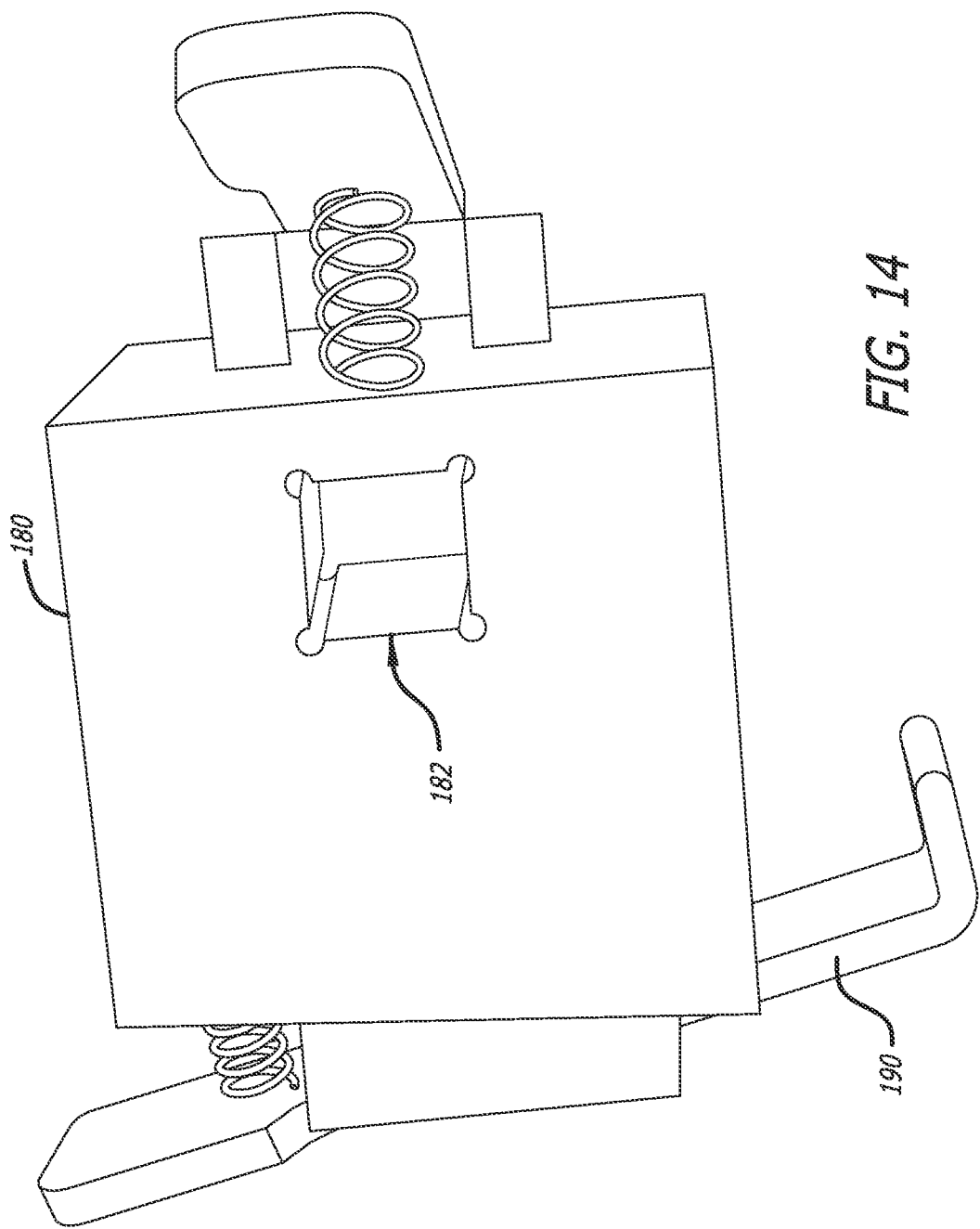
FIG. 14 is a top plan view of the top arm holder of the self-retaining retractor of FIG. 1A.
Figure 15:
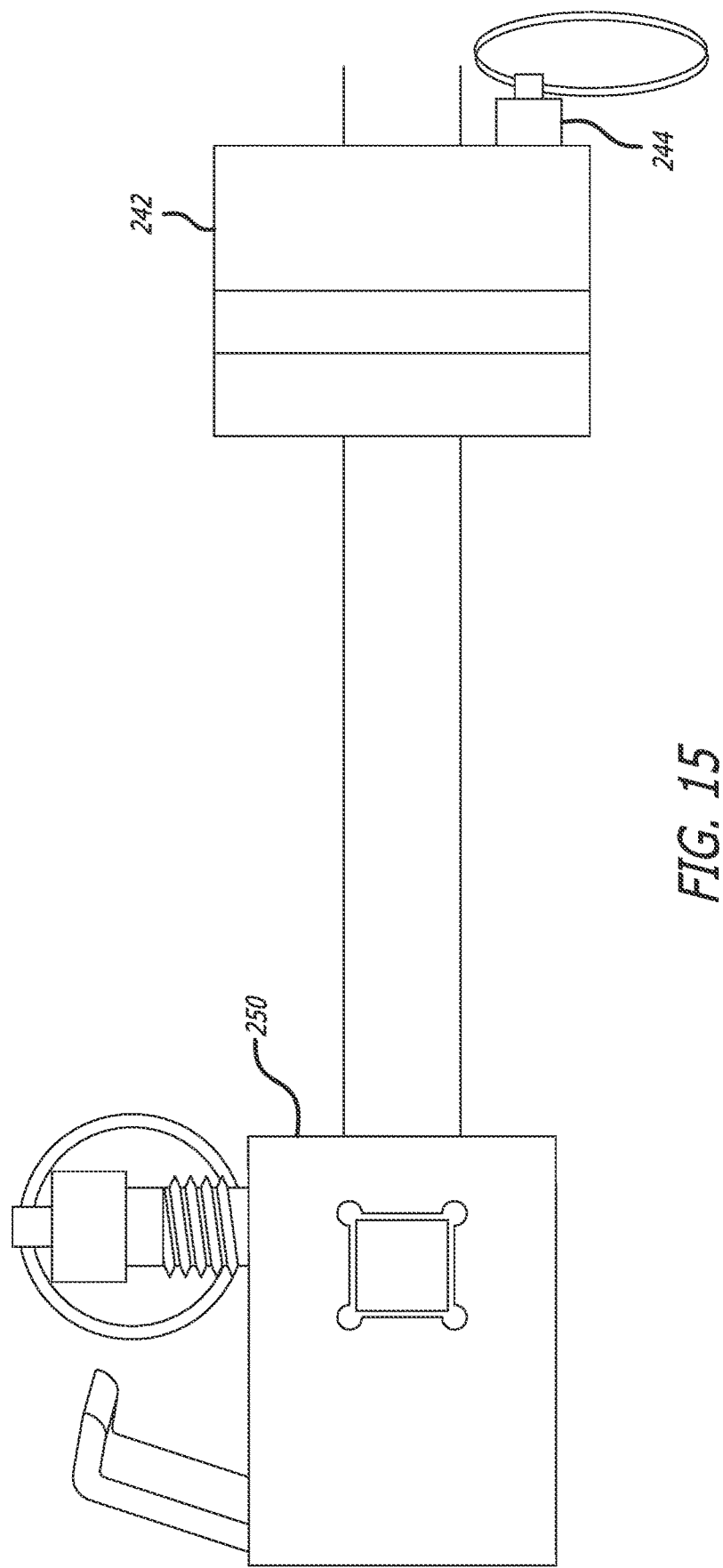
FIG. 15 is a top plan view of the top blade holder of the self-retaining retractor of FIG. 1A.

As shown in FIGS. 1A, 1B, 2, 8, 9, 11, and 13, vertical ratchet lock (180) is preferably in the configuration of a cubical block with a hole (182) to facilitate its movement up and down on the vertical lateral retractor poles (120, 122) and an aperture (184) to facilitate the movement of horizontal arm (140, 142). As can be seen in FIG. 14, both up and down and lateral movements can be locked into position with a locking mechanism (190) such as square teeth pawl for example. Preferably, there are two vertical ratchet locks (180) used for two lateral retractor blades (150, 152) and another vertical ratchet lock (180) used for upper horizontal ratchet arm (240).

As shown in FIGS. 1A, 1B, vertical arm ratchet (220) preferably includes a single horizontal lateral retractor blade (210) which can be utilized to hold in a raised position the bladder of a patient and protect it during surgery and eliminates the need for another assistant's hand to hold and protect the bladder during surgery. Handle (232) has ratchets to move horizontal angular retractor blade (210) up or down to a desired position and then locked with a locking mechanism (250).

As shown in FIGS. 1A, 1B, 1E, 13 and 15, upper horizontal ratchet arm (240) preferably includes at one end a connector in the configuration of a cylindrical connector (242) which is helpful in angling the tip of upper horizontal angular retractor blade (210) up or down depending on the need of exposure during surgery. In a preferred embodiment, cylindrical mechanism (242) rotates about its central axis to place upper horizontal angular retractor blade (210) in a desired position. Cylindrical connector (242) then can be locked in the desired position with a releasable pin (244) cooperatively engaging a receiving portion of cylindrical mechanism (242) to prevent rotation while pin (244) is engaged. Pin (244) can be part of a spring-actuated locking mechanism within cylindrical mechanism (242). In addition, there are ratchets (234) on upper horizontal arm (240) to move horizontal angular retractor blade (210) medially or laterally as required or desired by the surgeon.

As shown in FIGS. 1B, horizontal left and right lateral retractor blades (150, 152) preferably are 14 cm long and 4.5 cm wide with an 85 degree angle to the arm that attaches it to the lower horizontal arms (140, 142) through a semi-circular groove (174, 176). Different sizes of such retractor blades are available for use depending on the size of the patient surgical site such as, for example, narrowness of the vaginal opening or the depth of the vagina.

Figure 16:
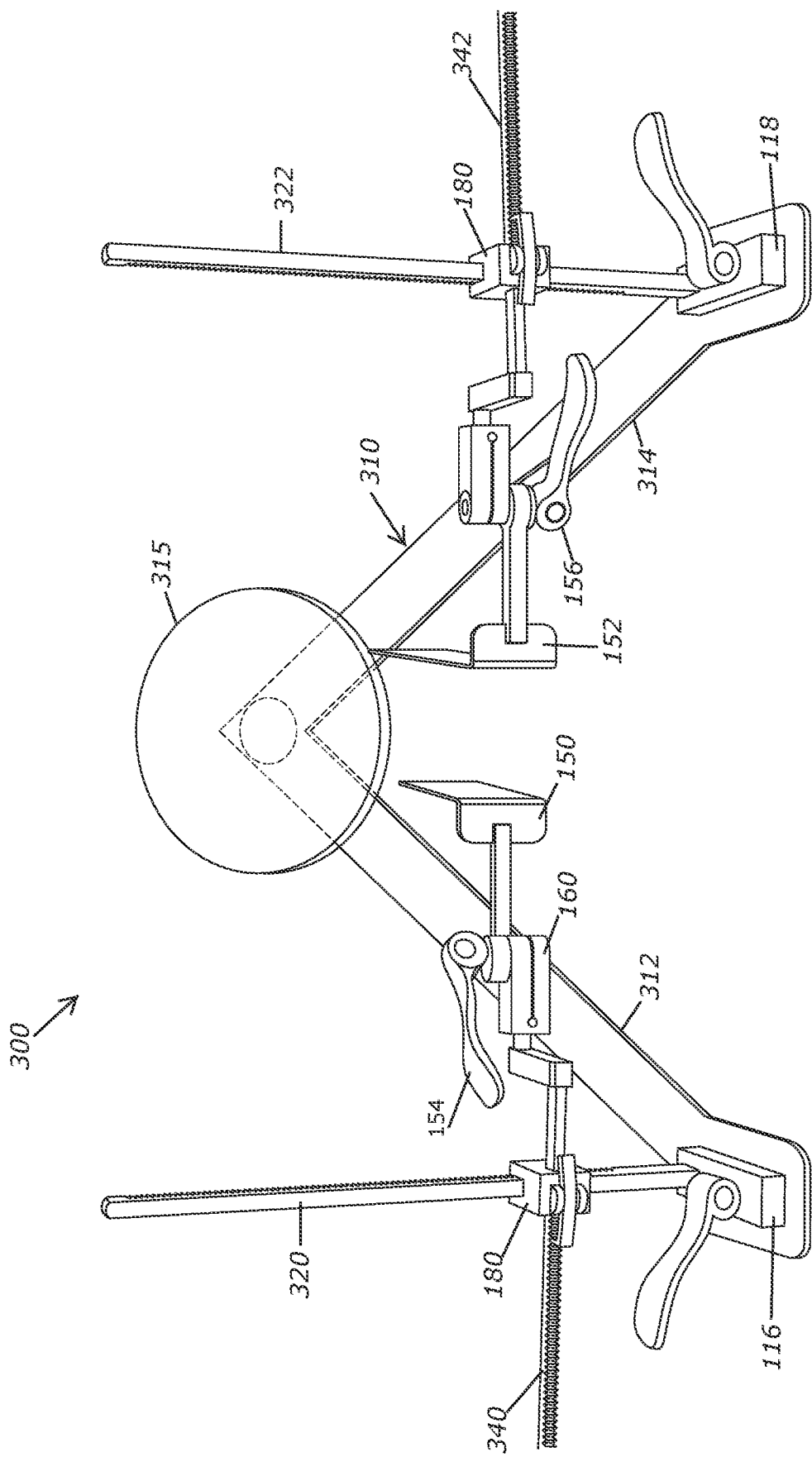
FIG. 16 is a front top perspective view of another embodiment of an assembled self-retaining retractor in accordance with the present invention.
Figure 17:
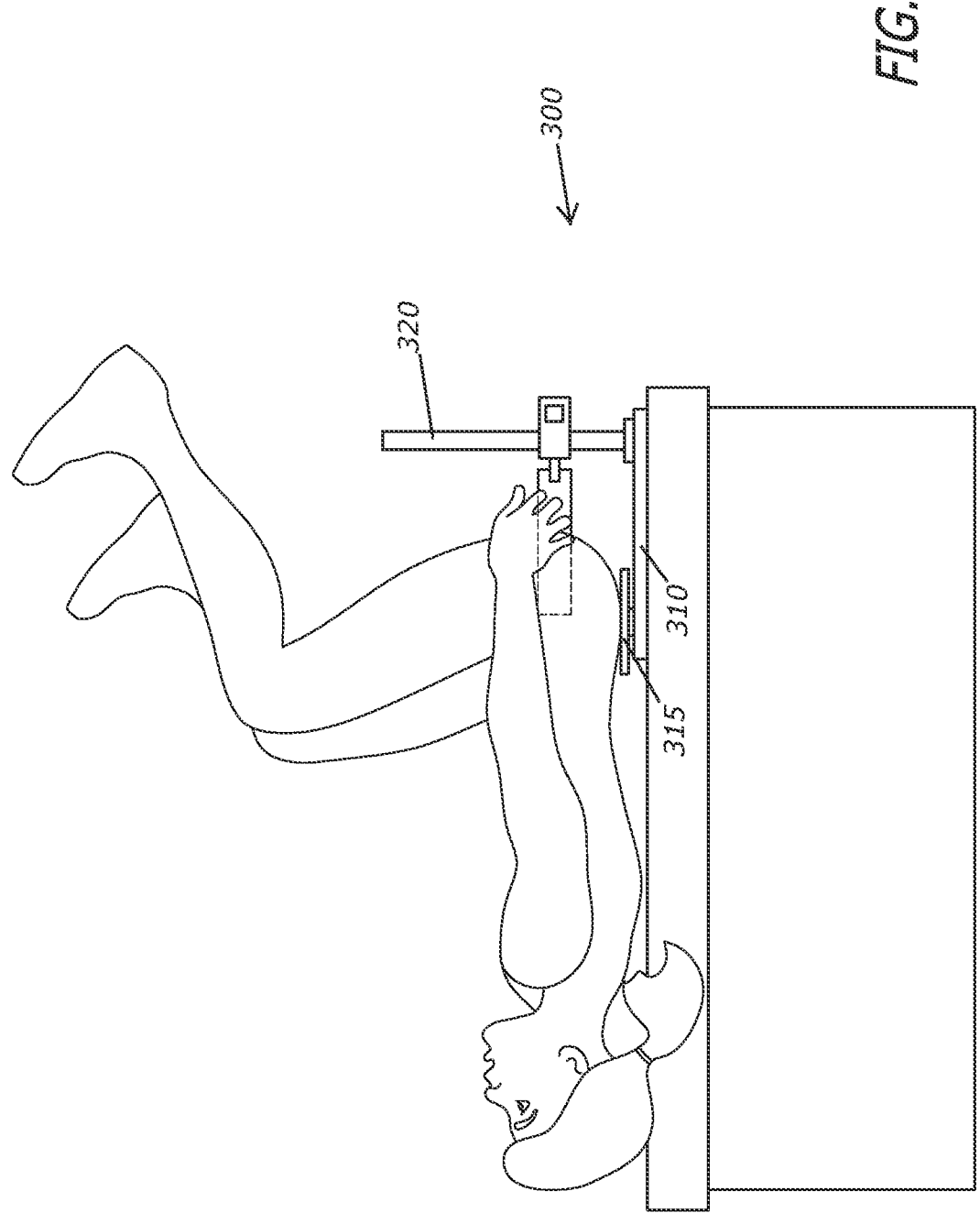
FIG. 17 is a side elevational view of a patient in the lithotomy position positioned on the self-retaining retractor of FIG. 16 and on an operating table

FIGS. 16 and 17 show another embodiment of retractor assembly (300) in accordance with the present invention. Retractor assembly (300) has a similar structure and configuration as retractor assembly (100) except that the base frame (310) has left and right arms (312, 314) positioned in a generally v-shaped configuration with their ends joined at one end below a turntable-style rotating disc (315) capable of rotating relative to the rest of base frame (310). In use, base frame (310) with rotating disc (315) is positioned under a patient's buttocks area such that the weight of the patient holds base frame (310) in a desired position relative to the patient, but disc (315) allows for controlled movement of arms (312, 314) relative to each to allow for adjustable positioning of retractor assembly (300) relative to the patient. Once the desired position base frame (310) is achieved, arms (312, 314) could be locked relative to each other to maintain the desired spacing suitable for use in the surgical procedure being performed. For example, a desired spacing apart of arms (312, 314) could be approximately 12 inches.

Figure 5:
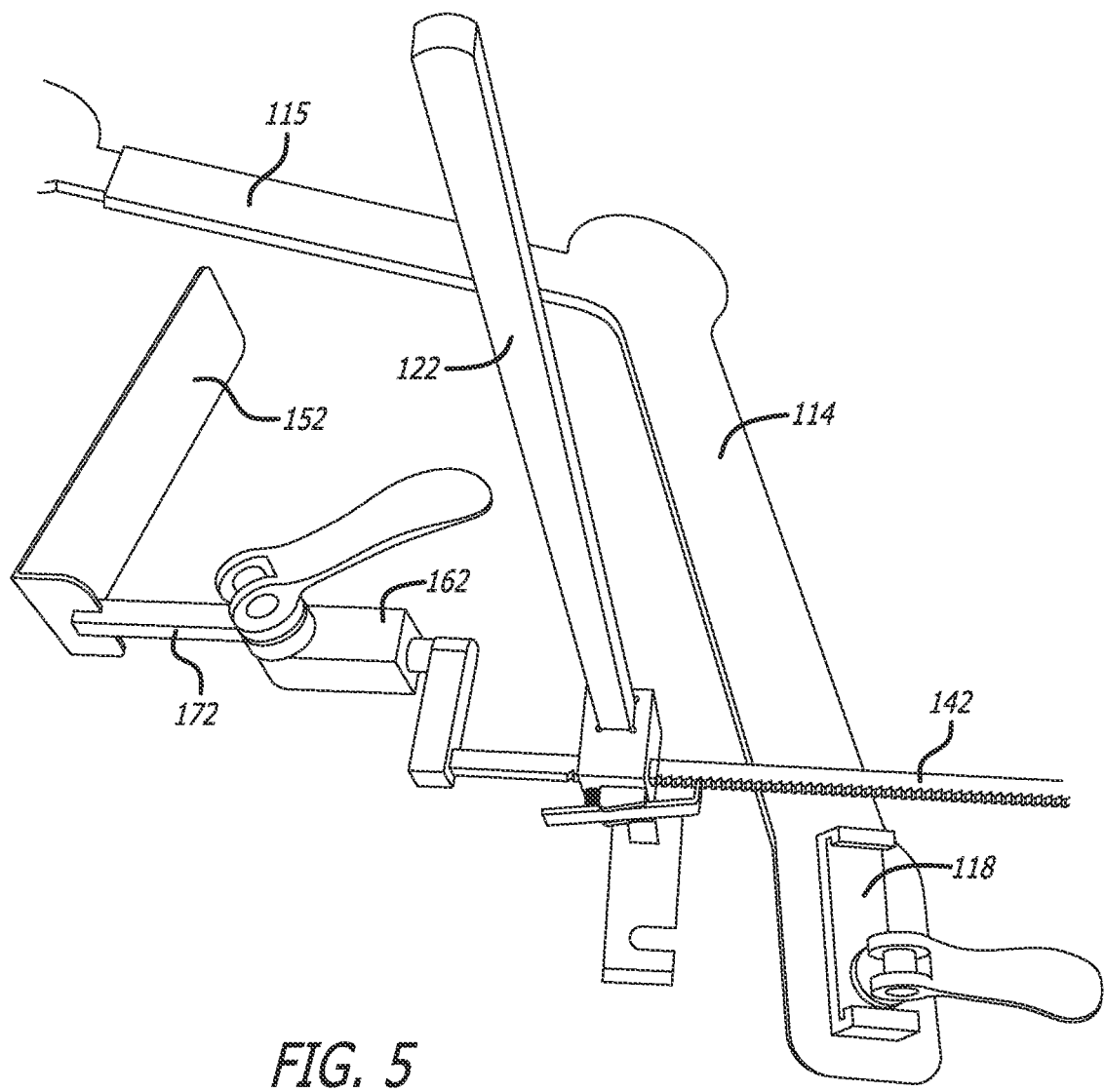
FIG. 5 is a partial top plan view of a disassembled vertical lateral retractor pole, horizontal arm, lateral retractor blade, and base plate section of the self-retaining retractor of FIG. 1A.
Figure 6:
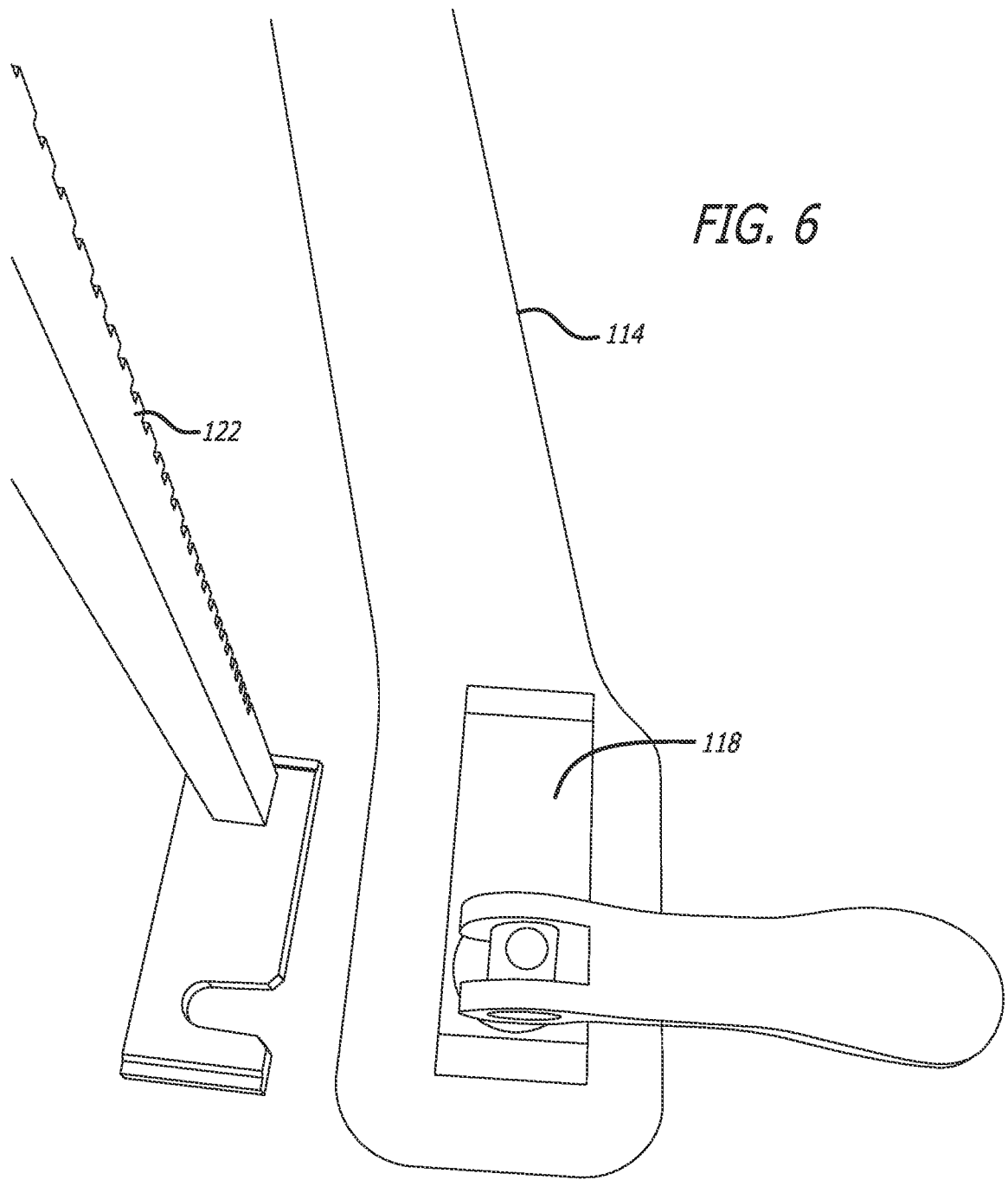
FIG. 6 is an enlarged, partial top plan view of a right vertical lateral retractor pole and right base plate section of the self-retaining retractor of FIG. 1A.
Figure 7:
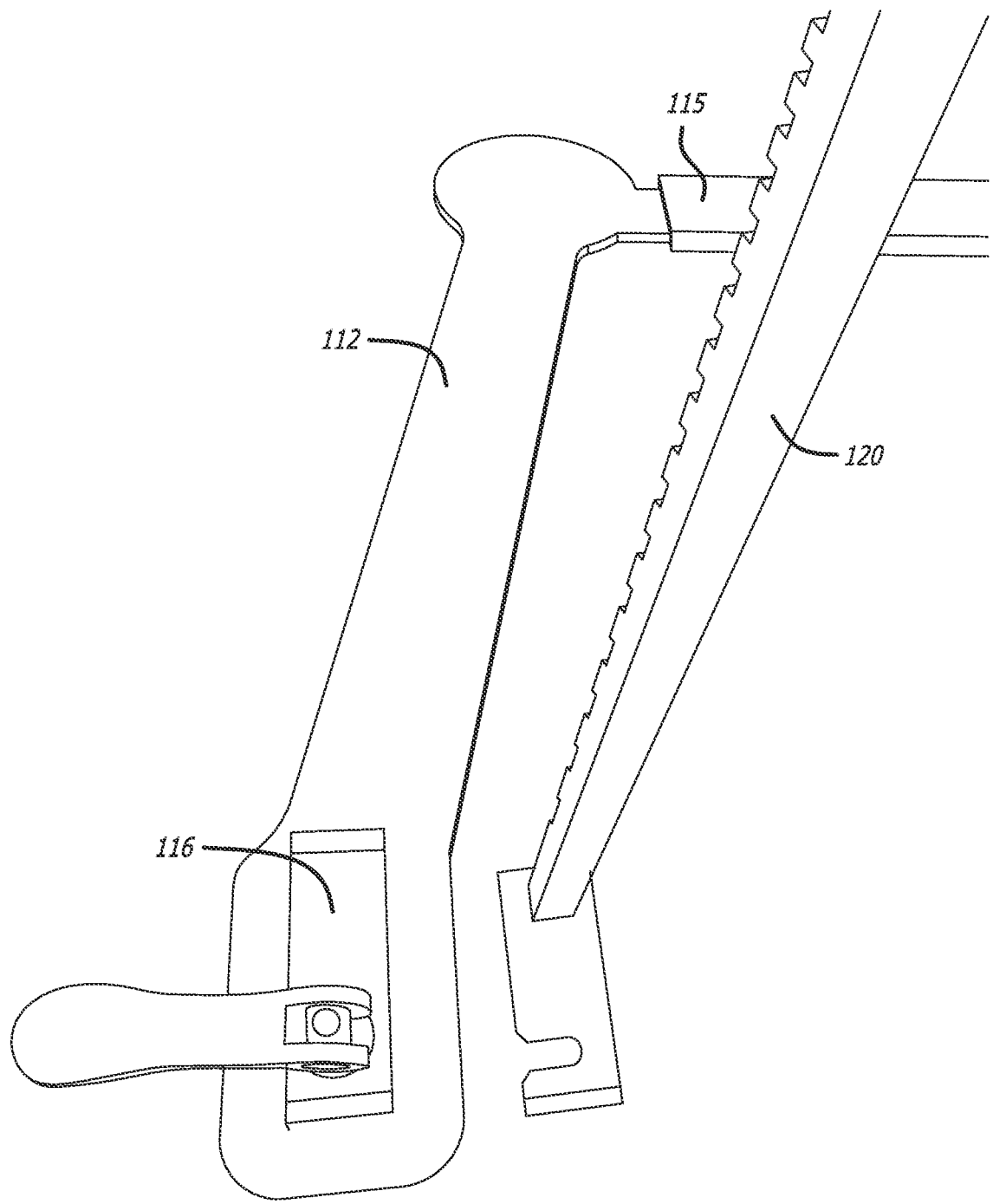
FIG. 7 is an enlarged, partial top plan view of a left vertical lateral retractor pole and left base plate section of the self-retaining retractor of FIG. 1A.
Figure 8:
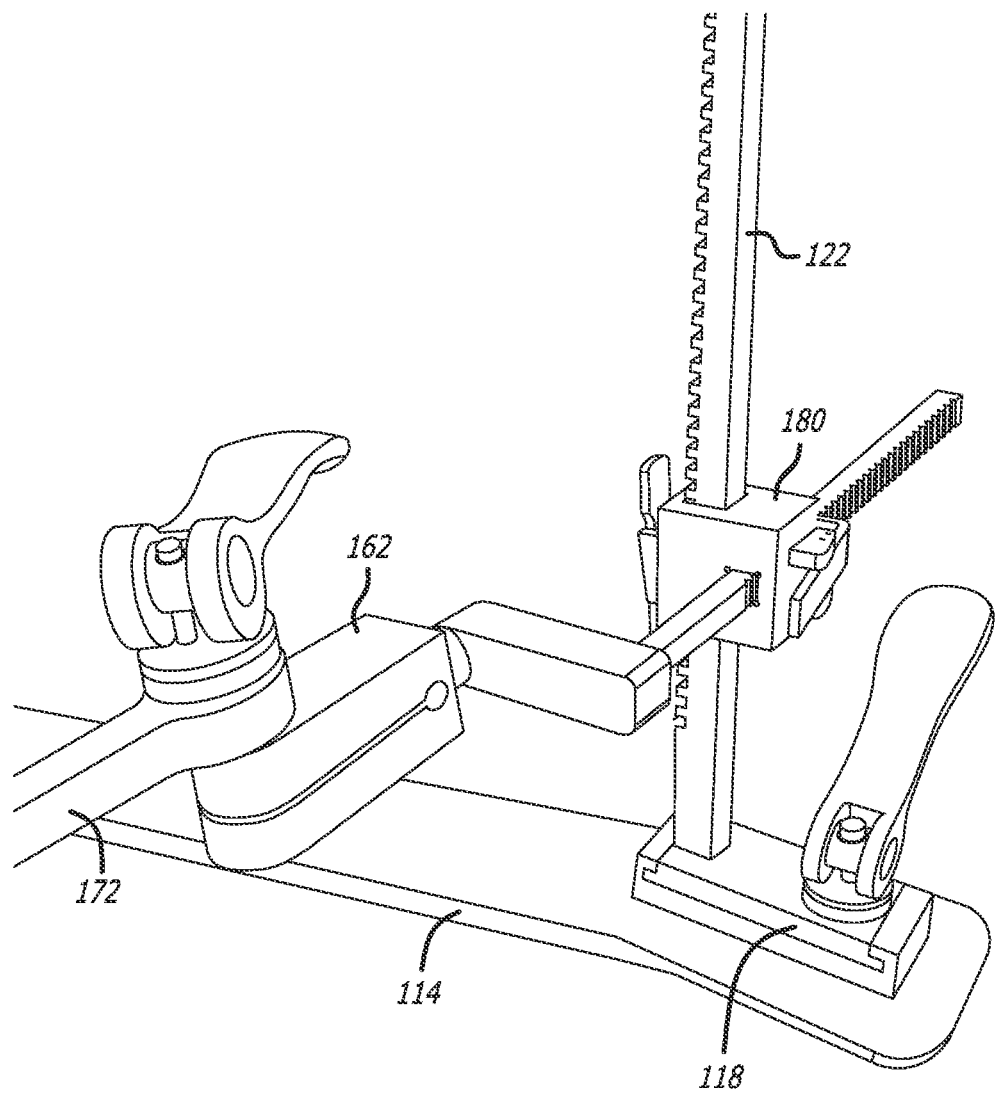
FIG. 8 is an enlarged, partial elevational view of the right vertical lateral retractor pole assembled to the right base plate section of the self-retaining retractor of FIG. 1A.
Figure 9:
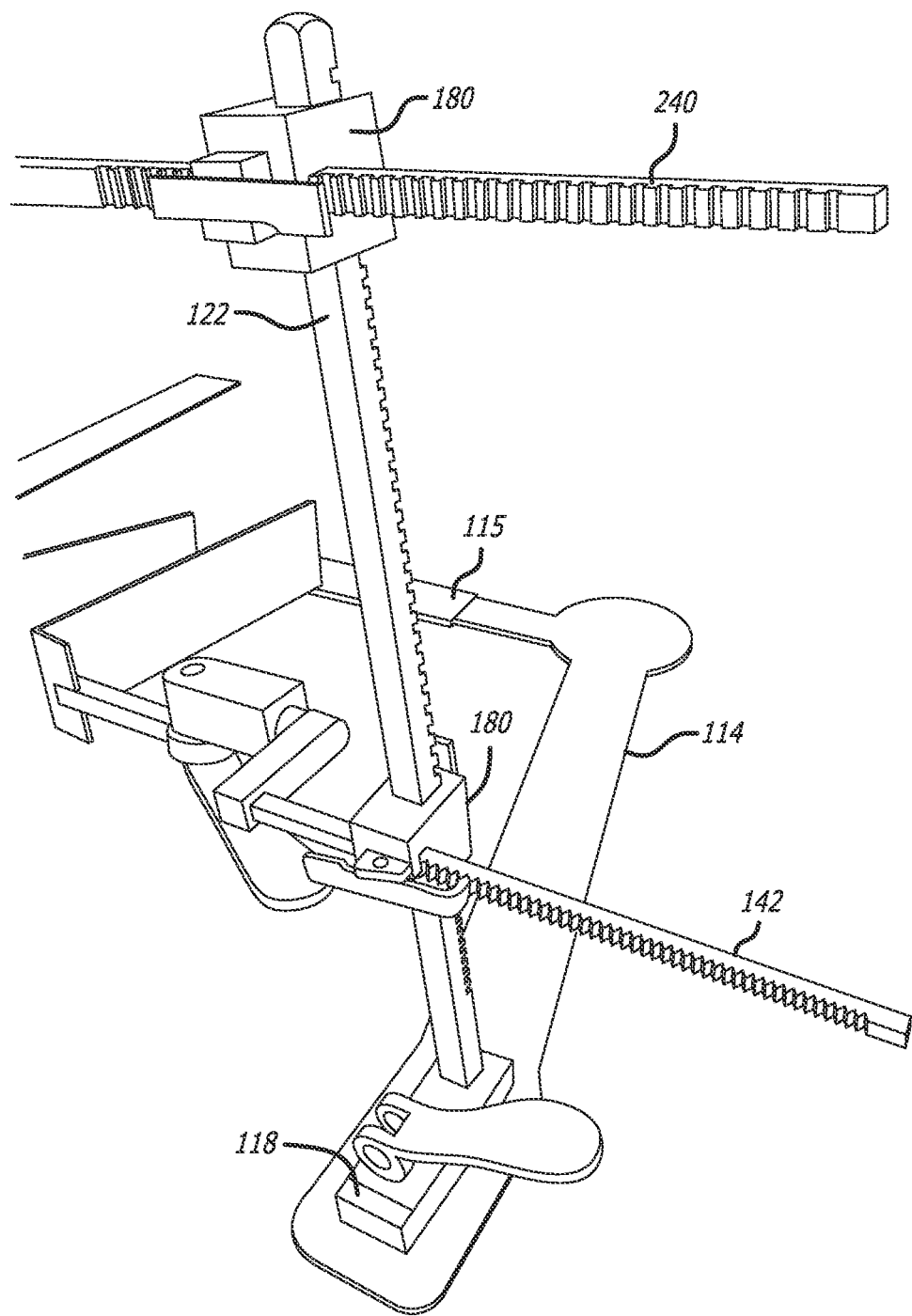
FIG. 9 is an enlarged, partial elevational view of the right vertical lateral retractor pole with horizontal arm and top arm assembled to the right base plate section of the self-retaining retractor of FIG. 1A.
Figure 10:
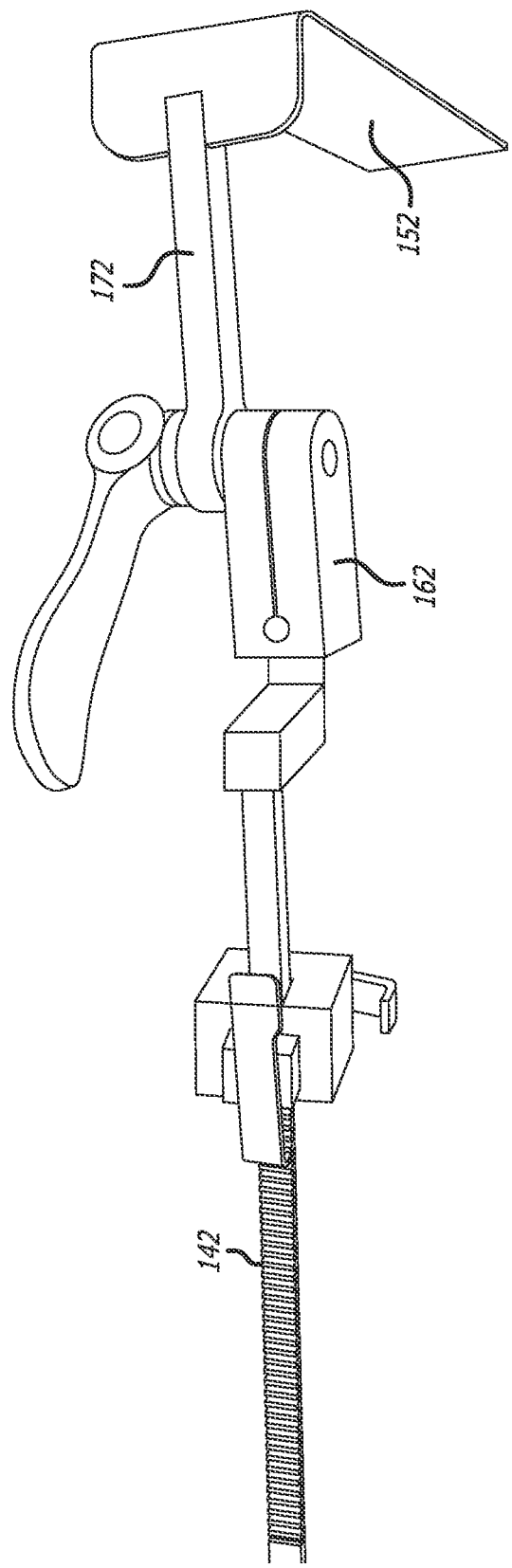
FIG. 10 is a top perspective view of an assembled horizontal arm, lateral blade holder and lateral retractor blade of the self-retaining retractor of FIG. 1A.
Figure 11:
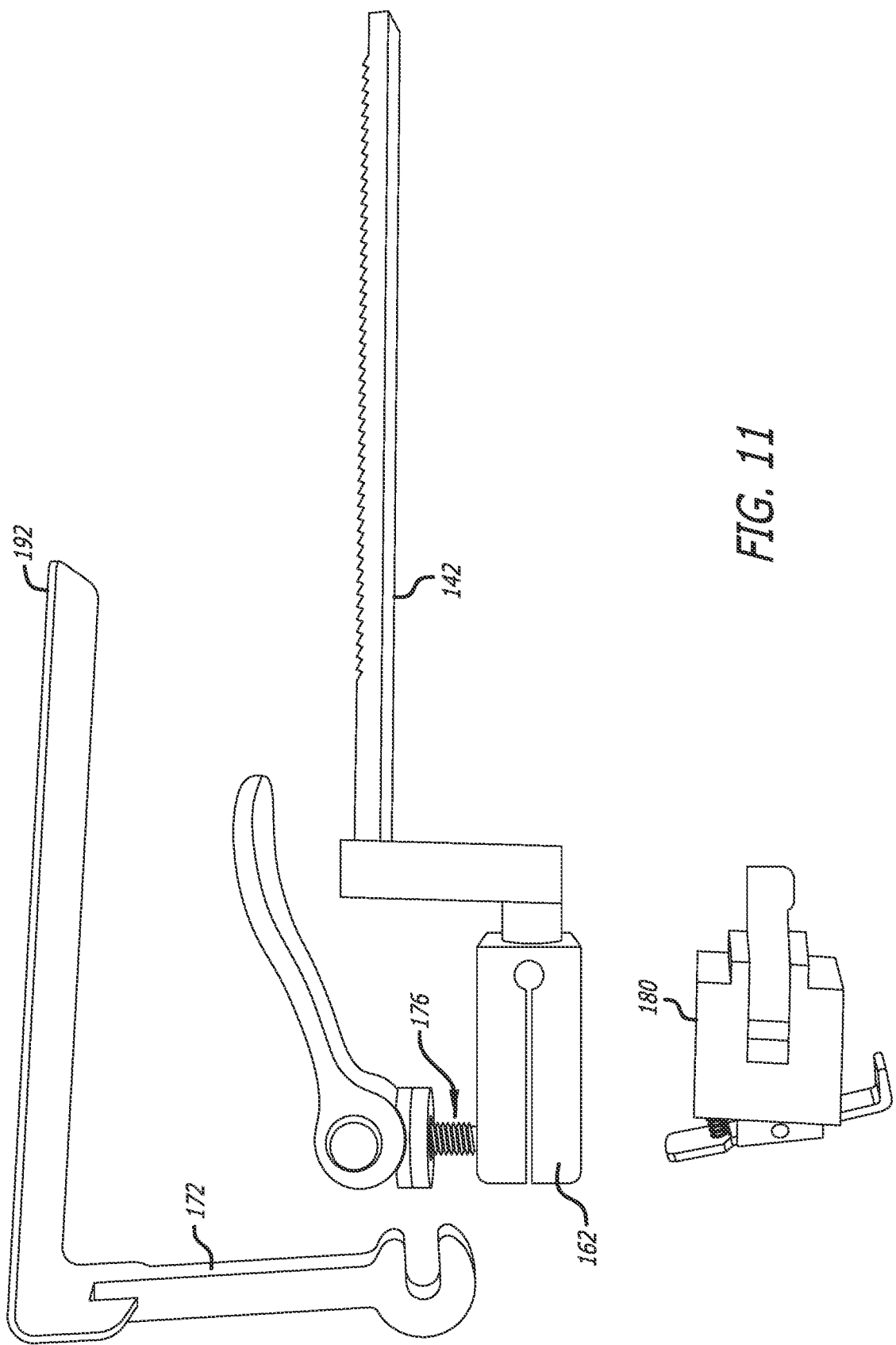
FIG. 11 is a disassembled top plan view of a horizontal arm, lateral blade holder, lateral retractor blade, and lateral arm holder of the self-retaining retractor of FIG. 1A.
Figure 12:
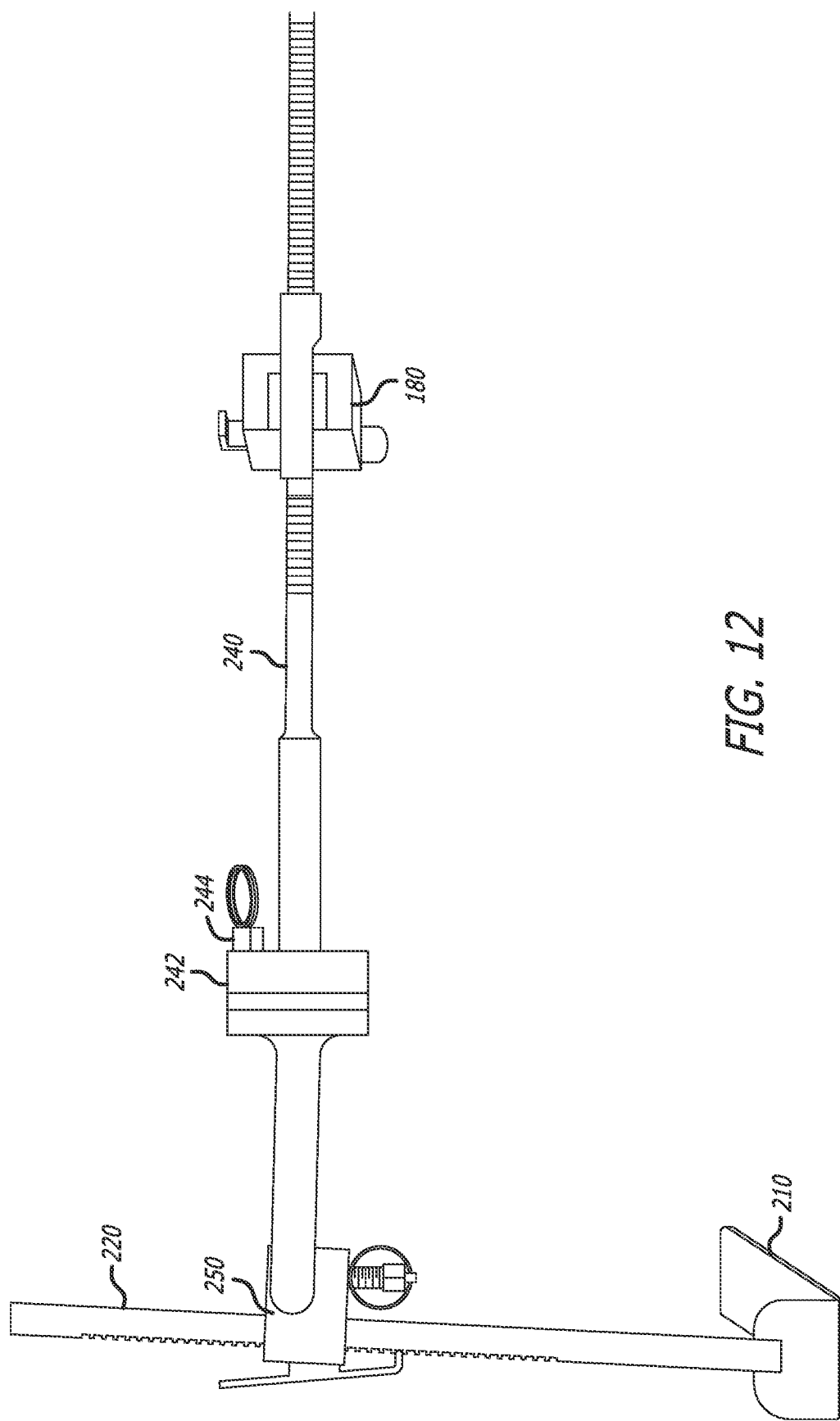
FIG. 12 is a top plan view of an assembled horizontal arm, top blade holder and top blade of the self-retaining retractor of FIG. 1A.
Figure 13:
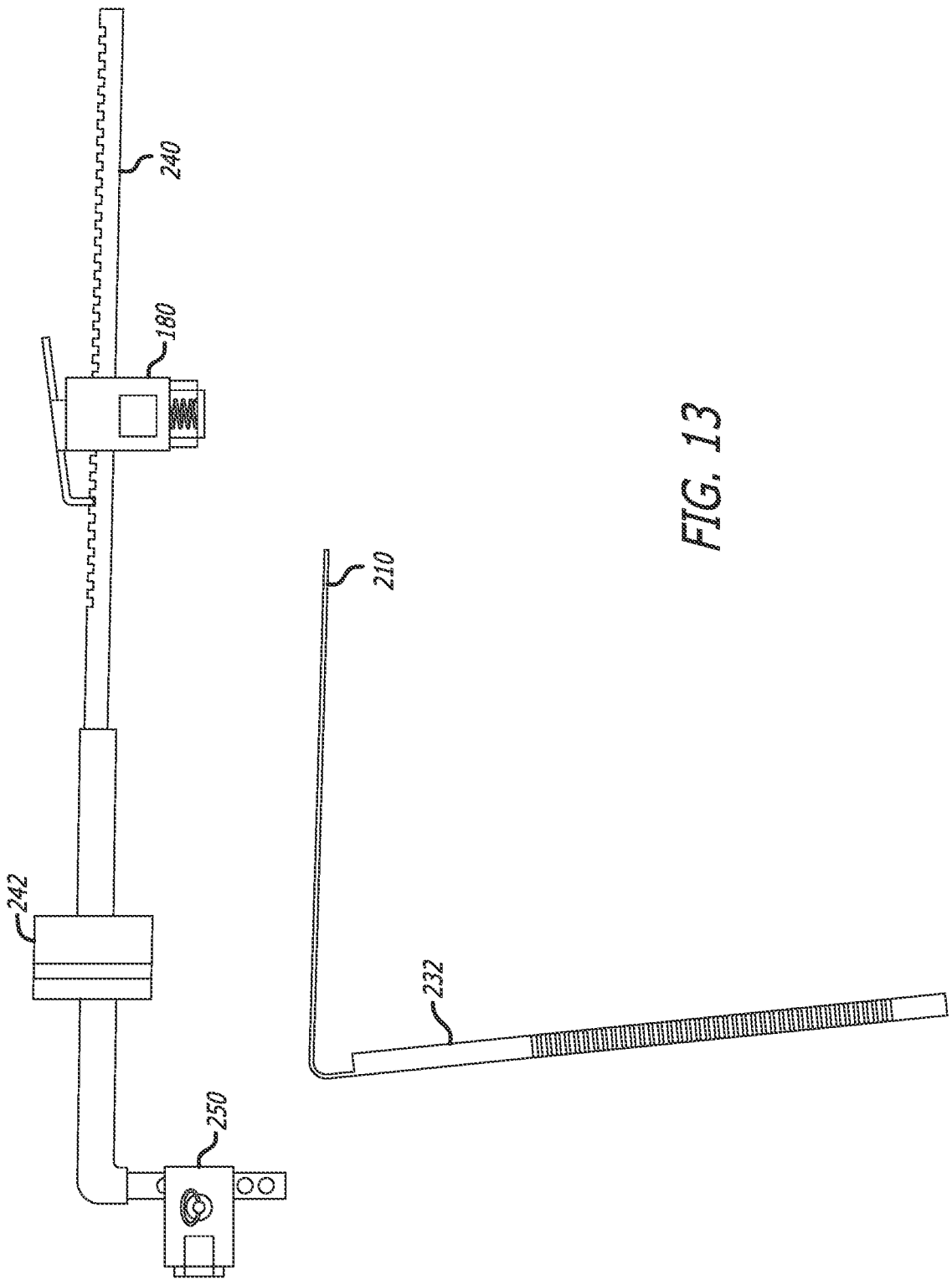
FIG. 13 is a top plan view of a partially disassembled horizontal arm, top blade holder and top blade of the self-retaining retractor of FIG. 1A.

Lateral vertical ratchet arms (320, 322) are similar to lateral vertical ratchet arms (120, 122) described above for retractor assembly (100). Lateral vertical ratchet arms (320, 322) are connected base frame (310) and locked in position via a foot locking mechanism for the foot of arms (320, 322). Lateral ratchet arms (320, 322) slide into the "foot" portion of base frame (310) for locking into position and easy removal in a similar manner as shown in FIG. 5, Lower horizontal arms (340,342) are attached to lateral vertical ratchet arms (320, 322) with a sliding lock with lever for example.

In an embodiment of base frame (310), each of arms (312, 314) has a length of approximately 10 inches, a width of approximately 1 inch, and a thickness of approximately ¼ inch. Each of lateral vertical ratchet arms (320, 322) has a length of approximately 6 inches, a width of approximately ½ inch, and a thickness of approximately ¼ inch. Disc (315) preferably has a diameter of approximately 8 inches and is supported by a rotating mechanism such as a bearing, axle or other mechanism suitable for the intended purpose of providing rotation of disc (315). The size and configuration of retractor assembly (300) provides a less bulky embodiment that is easier to assemble for a disposable retractor.

Figure 18:
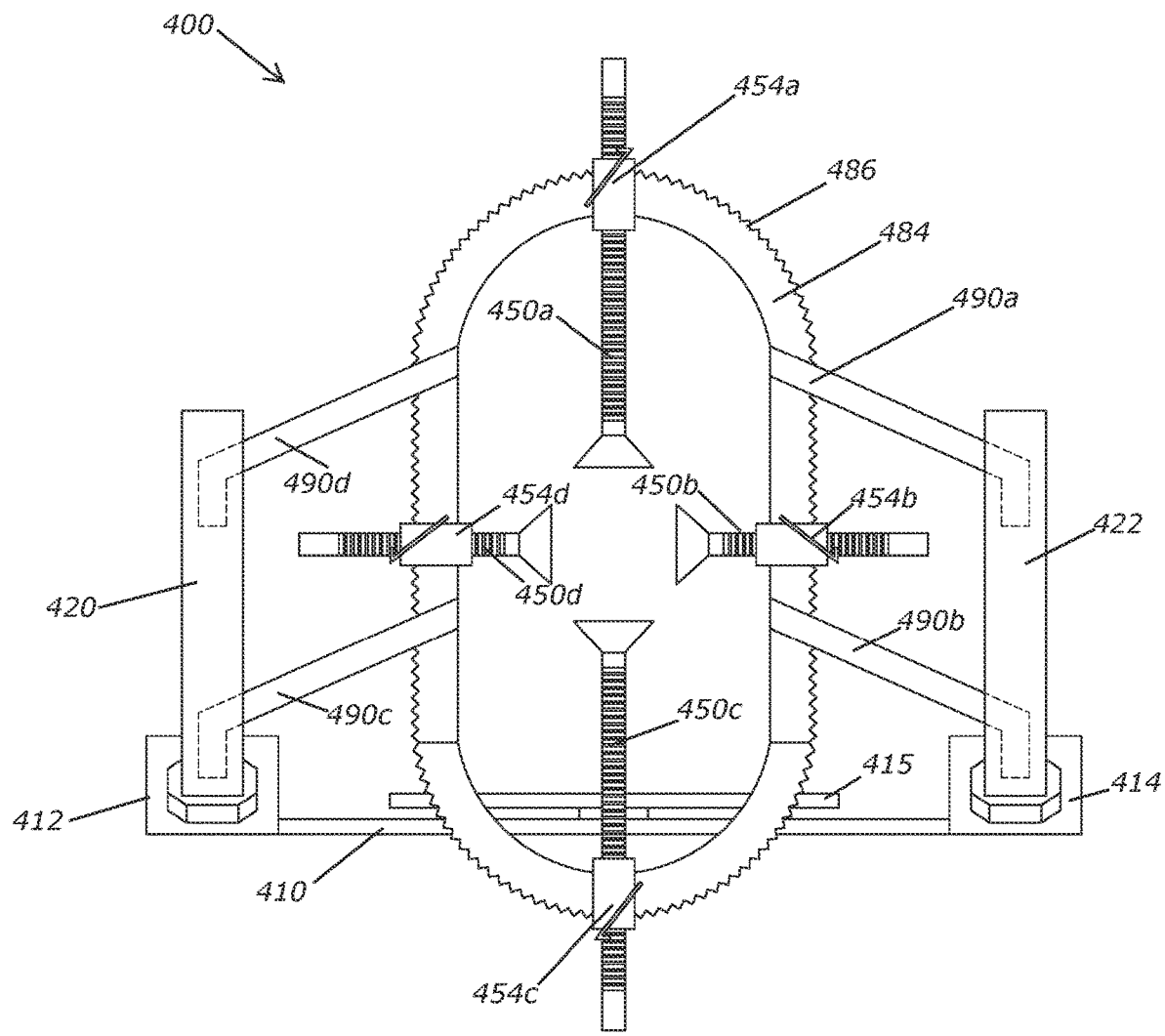
FIG. 18 is a front elevational view of yet another embodiment of an assembled self-retaining retractor in accordance with the present invention.
Figure 19:
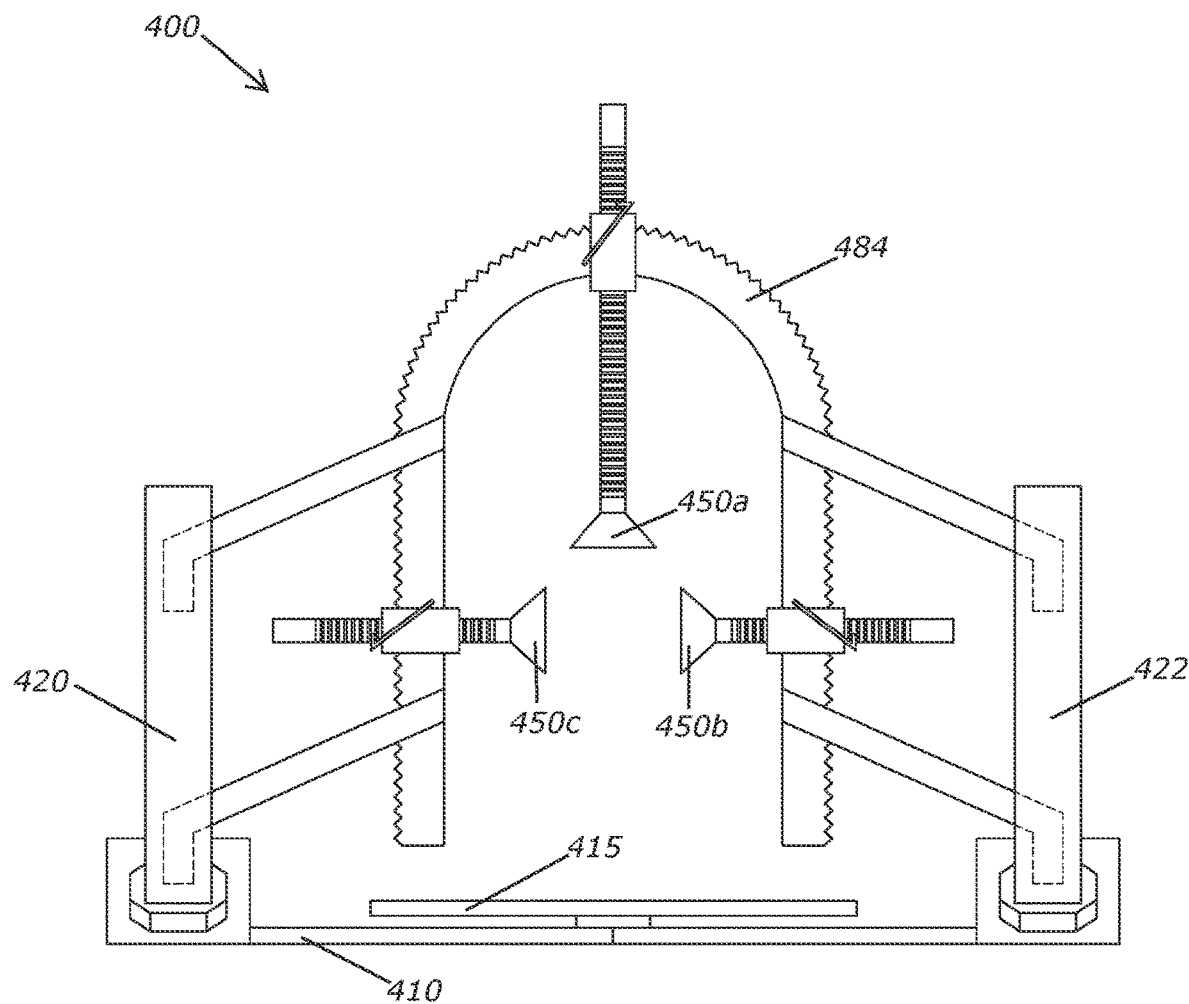
FIG. 19 is a front elevational view of the embodiment of an assembled self-retaining retractor of FIG. 18 with the bottom portion removed.

FIGS. 18 and 19 show yet another embodiment of retractor assembly (400) in accordance with the present invention. Retractor assembly (400) has a similar structure and configuration as retractor assembly (100) and retractor assembly (300). Base frame (410) is similar to base frame (310) has left and right arms (412, 414) positioned in a generally v-shaped configuration with their ends joined at one end below a turntable-style rotating disc (415) similar to disc (315), all relevant features described above being incorporated by reference herein.

Retractor assembly (400) preferably includes lateral vertical arms (420, 422) connected to base frame (410) and locked in position via a foot locking mechanism at the foot of arms (420, 422) similar to that described above for retractor assembly (300). An oval ring (484) has ratchets (486) along the outer edge of its external perimeter and has an open interior space for accessing a surgical site therethrough. Oval ring (484) is preferably similar to a Bookwalter-type ring that is used for abdominal self-retaining procedures. Retractor blades (450a-d) preferably are releasably secured to oval ring (484) via sliding locks (454a-d) with a release lever (456a-d) similar to Bookwalter locks. Retractor blades (450a-d) are positionable along the oval ring (484) as is suitable for the intended purpose of the surgical procedure being performed.

Oval ring (484) can be sized and dimensioned suitable for the patient site to be accessed during the surgical procedure, and for example for use in a gynecological procedure oval ring (484) preferably has a width of approximately 6 inches, a height of approximately 8 inches, and frame has a width of approximately ⅝ inch, and a thickness of approximately ¼ inch. Oval ring (484) is connected to lateral vertical arms (420, 422) by angled side arms (490a-d) that are also connected to oval ring (484) to either be removably attached or permanently secured (i.e. welded, fused) to oval ring (484). Side arms (490a-d) preferably have an inward angle (484) to push the Oval Ring towards the patient by approximately 1 inch.

Alternatively, oval ring (484), angled side arms (490a-d), and lateral vertical arms (420, 422) are connected to form a single unit that can be removably connected to the base frame (410). The single unit construction provides for a simple placement and replacement of oval ring (484) to base frame (410) and reduces assembly time compared to a multiple part system requiring each part to be individually assembled and attached. It is within the scope of the present invention that the construct of the oval ring (484), angled side arms (490a-d), and lateral vertical arms (420, 422) as a single unit be made of a material suitable for one time use and is disposable after use. This approach saves on the expense and time that would be required to clean and sterilize the components for repeated use. Examples of such material would include surgical quality metals, composites, and polycarbonate materials of sufficient structural strength suitable for the intended use during surgery. It is further appreciated this embodiment of the oval ring, angled side arms, and vertical arms as a single unit is not limited to use with frame (410) but can be used with the other base frames and base plates disclosed herein or other suitable alternatives without departing from the spirit and scope of the present invention.

As shown in FIG. 19, as an alternative, the bottom portion of oval ring (484) can be removed in circumstances where there is not enough clearance at the bottom portion and the bottom retractor cannot be used, such as when the patient is lying on the bed and is unable to be in a lithotomy position. When the patient s in the operating room in a lithotomy position, with the bottom at the end of the operating table there would be no problem using the full oval ring (484) with a bottom retractor blade.

The retractor assembly components and instruments being held are made of materials suitable for the intended use in a surgical procedure and may include, but are not limited to surgical grade stainless steel, titanium, composite materials and the like.

While the instrumentation and methods of the present invention have been described in reference to a preferred use is a gynecological procedure, it is appreciated that they are not so limited and that other procedures including urological and other surgical procedures can benefit from a self-retaining surgical retractor in accordance with the present invention.

The foregoing outlines features of several embodiments so that those of ordinary skill in the art may better understand various aspects of the present disclosure. Those of ordinary skill in the art should appreciate that they may readily use the present disclosure as a basis for designing or modifying other processes and structures for carrying out the same purposes and/or achieving the same advantages of various embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

Various operations of embodiments are provided herein. The order in which some or all of the operations are described should not be construed to imply that these operations are necessarily order dependent. Alternative ordering will be appreciated having the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or". In addition. "a" and "an" as used in this application and the appended claims are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising", Also, unless specified otherwise, "first," "second," or the like are not intended to imply a temporal aspect, a spatial aspect, an ordering, etc. Rather, such terms are merely used as identifiers, names, etc. for features, elements, items, etc. For example, a first element and a second element generally correspond to element A and element B or two different or two identical elements or the same element.

Also, although the disclosure has been shown and described with respect to one or more implementations, equivalent alterations and modifications will occur to others of ordinary skill in the art based upon a reading and understanding of this specification and the annexed drawings. The disclosure comprises all such modifications and alterations. In particular regard to the various functions performed by the above described features (e.g., elements, resources, etc.), the terms used to describe such features are intended to correspond, unless otherwise indicated, to any features which performs the specified function of the described features (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The invention claimed is:

1. A self-retaining surgical retractor assembly for use with a patient in a lithotomy position on a surgical table, the retractor assembly comprising:
    a plurality of surgical retractors each comprising a blade and a handle;
    a base plate comprising an upper surface and a lower surface, spaced apart first and second arms each having a leading end and an opposite trailing end, the first and second arms being coupled proximate the leading ends by a connector, the connector having a length that is moveably adjustable to permit modification of a separation distance between the first and second arms, the first and second arms extending from the connector and terminating at the trailing ends, the base plate being sized and configured for placement at least in part on the surgical table and under the patient in the lithotomy position on the surgical table, whereby when the base plate is positioned with the lower surface on the surgical table with the upper surface, the leading ends and connector beneath the buttocks of the patient, the trailing ends of the first and second arms extend to a positon located anterior to the patient to hold instruments at a position in front of the patient;
    left and right lateral vertical arms extending generally perpendicular from the upper surface of the first and second arms of the base plate, the left lateral vertical arm having one end releasably connected to the first arm of the base plate, the right lateral vertical arm having one end releasably connected to the second arm of the base plate;
    a left lower horizontal arm having a central longitudinal axis and a length terminating at an end coupled to a first of the surgical retractors, a right lower horizontal arm having a central longitudinal axis and a length terminating at an end coupled to a second of the surgical retractors;
    an upper horizontal arm having a central longitudinal axis and a length terminating at an end coupled to a third of the surgical retractors;
    a first lock having a first portion for movable attachment to the left vertical arm and a second portion for moveable attachment to the left lower horizontal arm, the left lower horizontal arm being held by the first lock in a position with its central longitudinal axis generally perpendicular to the central longitudinal axis of the left vertical arm;
    a second lock having a first portion for movable attachment to the right vertical arm and a second portion for moveable attachment to the right lower horizontal arm, the right lower horizontal arm being held by the second lock in a position with its central longitudinal axis generally perpendicular to the central longitudinal axis of the right vertical arm; and
    a third lock having a first portion for movable attachment to the right vertical arm and a second portion for moveable attachment to the upper horizontal arm, the upper horizontal arm being held by the third lock in a position with its central longitudinal axis generally perpendicular to the central longitudinal axis of the right vertical arm;
    whereby the vertical positioning of the first, second, and third surgical retractors can be adjusted by movement of the first, second, and third locks up and down along the height of the central axes of the vertical arms, respectively, and
    whereby the horizontal positioning of the first, second, and third surgical retractors can be adjusted by movement of the lower and upper horizontal arms along their central axes relative to the first, second, and third locks, respectively.

2. A self-retaining surgical retractor assembly for use with a patient in a lithotomy position on a surgical table, the retractor assembly comprising:
    a plurality of surgical retractors each comprising a blade and a handle;
    a base frame comprising an upper surface and a lower surface, spaced apart first and second arms each having a leading end and an opposite trailing end, the first and second arms being coupled by a rotational connector proximate the leading ends to form a v-shaped configuration, the first and second arms capable of rotational movement about the connector to permit modification of a separation distance between trailing ends of the first and second arms, the first and second arms extending from the connector and terminating at the trailing ends;

a rotating disc positioned above the leading ends of the first and second arms of the base frame over the connector, the rotating disc rotating relative to the base frame and independently of the first and second arms, the rotating disc have an upper surface to be placed in contact with the patient;

the base frame being sized and configured for placement at least in part on the surgical table and under the patient in the lithotomy position on the surgical table, whereby when the base frame is positioned with the lower surface on the surgical table with the upper surface, the leading ends and the rotating disc beneath the buttocks of the patient, the trailing ends of the first and second arms extend to a positon located anterior to the patient to hold instruments at a position in front of the patient;

left and right lateral vertical arms extending generally perpendicular from the upper surface of the first and second arms of the base frame, the left lateral vertical arm having one end releasably connected to the first arm of the base frame, the right lateral vertical arm having one end releasably connected to the second arm of the base frame;

a left lower horizontal arm having a central longitudinal axis and a length terminating at an end coupled to a first of the surgical retractors, a right lower horizontal arm having a central longitudinal axis and a length terminating at an end coupled to a second of the surgical retractors;

a first lock having a first portion for movable attachment to the left vertical arm and a second portion for moveable attachment to the left lower horizontal arm, the left lower horizontal arm being held by the first lock in a position with its central longitudinal axis generally perpendicular to the central longitudinal axis of the left vertical arm;

a second lock having a first portion for movable attachment to the right vertical arm and a second portion for moveable attachment to the right lower horizontal arm, the right lower horizontal arm being held by the second lock in a position with its central longitudinal axis generally perpendicular to the central longitudinal axis of the right vertical arm; and whereby the vertical positioning of the first and second surgical retractors can be adjusted by movement of the first and second locks up and down along the height of the central axes of the vertical arms, respectively, and whereby the horizontal positioning of the first and second surgical retractors can be adjusted by movement of the lower and upper horizontal arms along their central axes relative to the first and second locks, respectively.

3. The surgical retractor assembly of claim 2 further comprising an upper horizontal arm having a central longitudinal axis and a length terminating at an end coupled to a third of the surgical retractors.

4. The surgical retractor assembly of claim 3 further comprising a third lock having a first portion for movable attachment to the right vertical arm and a second portion for moveable attachment to the upper horizontal arm, the upper horizontal arm being held by the third lock in a position with its central longitudinal axis generally perpendicular to the central longitudinal axis of the right vertical arm.

5. A self-retaining surgical retractor assembly for use with a patient in a lithotomy position on a surgical table, the retractor assembly comprising:

a plurality of surgical retractors each comprising a blade and a handle;

a base frame comprising an upper surface and a lower surface, spaced apart first and second arms each having a leading end and an opposite trailing end, the first and second arms being coupled by a rotational connector proximate the leading ends to form a v-shaped configuration, the first and second arms capable of rotational movement about the connector to permit modification of a separation distance between trailing ends of the first and second arms, the first and second arms extending from the connector and terminating at the trailing ends;

a rotating disc positioned above the leading ends of the first and second arms of the base frame over the connector, the rotating disc rotating relative to the base frame and independently of the first and second arms, the rotating disc have an upper surface to be placed in contact with the patient;

the base frame being sized and configured for placement at least in part on the surgical table and under the patient in the lithotomy position on the surgical table, whereby when the base frame is positioned with the lower surface on the surgical table with the upper surface, the leading ends and the rotating disc beneath the buttocks of the patient, the trailing ends of the first and second arms extend to a positon located anterior to the patient to hold instruments at a position in front of the patient;

left and right lateral vertical arms extending generally perpendicular from the upper surface of the first and second arms of the base frame, the left lateral vertical arm having one end releasably connected to the first arm of the base frame, the right lateral vertical arm having one end releasably connected to the second arm of the base frame;

a ring having an open interior space for accessing a surgical site there through, ring is connected to angled side arms that are that are also connected to left and right vertical arms; and retractor blades are releasably secured to the ring via sliding locks, retractor blades are positionable along the ring as is suitable for the intended purpose of the surgical procedure being performed.

6. The surgical retractor assembly of claim 5, wherein the ring has ratchets along the outer edge of its external perimeter.

7. The surgical retractor assembly of claim 5, wherein the ring includes at east a portion thereof that is removable.

8. The surgical retractor assembly of claim 7, wherein a bottom portion of the ring is removable.

* * * * *